United States Patent [19]
Walsh

[11] Patent Number: 5,858,990
[45] Date of Patent: Jan. 12, 1999

[54] FAS LIGAND COMPOSITIONS FOR TREATMENT OF PROLIFERATIVE DISORDERS

[75] Inventor: Kenneth Walsh, Carlisle, Mass.

[73] Assignee: St. Elizabeth's Medical Center, Boston, Mass.

[21] Appl. No.: 810,453

[22] Filed: Mar. 4, 1997

[51] Int. Cl.$^6$ .......................... A61K 48/00; C12N 15/11
[52] U.S. Cl. .......................... 514/44; 435/6; 435/172.1; 435/320.1; 435/69.1; 435/375; 435/377
[58] Field of Search .......................... 435/6, 172.1, 172.3, 435/320.1, 325, 69.1, 31.1, 375, 377; 536/23.1, 23.5; 514/2, 44

[56] References Cited

U.S. PATENT DOCUMENTS

| | | | |
|---|---|---|---|
| 5,219,740 | 6/1993 | Miller et al. | 435/69 |
| 5,563,039 | 10/1996 | Goeddel et al. | 435/7.1 |

FOREIGN PATENT DOCUMENTS

| | | |
|---|---|---|
| 0 675 200 A1 | 10/1995 | European Pat. Off. . |
| WO94/20625 | 9/1994 | WIPO . |
| WO95/32627 | 1/1995 | WIPO . |
| WO95/13293 | 5/1995 | WIPO . |
| WO95/31544 | 11/1995 | WIPO . |
| WO96/06111 | 2/1996 | WIPO . |
| WO96/25941 | 8/1996 | WIPO . |
| WO94/40864 | 12/1996 | WIPO . |
| WO97/02290A | 1/1997 | WIPO . |

OTHER PUBLICATIONS

Tanaka, M., et al., "Expression of the Functional Soluble Form of Human Fas Ligand in Activated Lymphocytes", *The EMBO Journal*, (1995), 14:6:1129–1135.

Han, D. K., et al., "Evidence for Escape of Apoptosis by Loss of Fas in Atherosclerotic Plaque Smooth Muscle Cells", *Supplement 1–Circulation*, (1996) 94:6, Abstract 2311.

Alvarez, R.J., et al., "Induction of Fas in Pertussis Toxin Treated Endothelial Cells: Implications for . . . Apoptosis", *Supplement 1–Circulation*, (1996) 94:6, Abstract 0590.

Bishopp Frances, "Ceres' Research Explores Use of Fas Ligand in Immune System Suppression, Tumors", *Bioworld Today*, (1996), 7:252:1.

Orkin et al "Report and Reccomendations of the Panel to Asses the NIH Investment in Research on Gene Therapy", Dec. 7, 1995.

Takahashi, T. Mol Human Fas Ligand: Gene Structure, Chromosomal Location and Species Specificity: International Immunology vol. 6(10): 1567–1574, 1994.

Mita, E. et al "Role of Fas Ligand in Apoptosis Induced by Hepatitis C Virus Infection." Biochemical and Biophysical Research Communications vol. 204(2):468–474, Oct. 28, 1994.

Primary Examiner—George C. Elliott
Assistant Examiner—Sean McGarry
Attorney, Agent, or Firm—Wolf, Greenfield & Sacks, P.C.

[57] ABSTRACT

A method for treating vascular injury, particularly vascular injury resulting from restenosis following angioplasty, and vascular remodeling is provided. The method involves administering to subjects in need of such treatment an effective amount of a Fas ligand molecule.

9 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1790 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 86..931

( i x ) FEATURE:
        ( A ) NAME/KEY: "transmembrane domain, amino acids 81-102"
        ( B ) LOCATION: 326..391

( i x ) FEATURE:
        ( A ) NAME/KEY: "potential N-linked glycocylation site,
            amino acid 184"
        ( B ) LOCATION: 635..637

( i x ) FEATURE:
        ( A ) NAME/KEY: "potential N-linked glycocylation site,
            amino acid 250"
        ( B ) LOCATION: 833..835

( i x ) FEATURE:
        ( A ) NAME/KEY: "potential N-linked glycocylation site,
            amino acid 260"
        ( B ) LOCATION: 863..865

( x i ) SEQUENCE DESCRIPTION: SEQ ID NO:1:

```
GGGTCCCGTC  CTTGACACCT  CAGCCTCTAC  AGGACTGAGA  AGAAGTAAAA  CCGTTTGCTG          60

GGGCTGGCCT  GACTCACCAG  CTGCC ATG CAG CAG CCC TTC AAT TAC CCA TAT              112
                              Met Gln Gln Pro Phe Asn Tyr Pro Tyr
                              1                 5

CCC CAG ATC TAC TGG GTG GAC AGC AGT GCC AGC TCT CCC TGG GCC CCT                160
Pro Gln Ile Tyr Trp Val Asp Ser Ser Ala Ser Ser Pro Trp Ala Pro
 10              15                  20                  25

CCA GGC ACA GTT CTT CCC TGT CCA ACC TCT GTG CCC AGA AGG CCT GGT                208
Pro Gly Thr Val Leu Pro Cys Pro Thr Ser Val Pro Arg Arg Pro Gly
                 30              35                  40

CAA AGG AGG CCA CCA CCA CCA CCG CCA CCG CCA CCA CTA CCA CCT CCG                256
Gln Arg Arg Pro Pro Pro Pro Pro Pro Pro Pro Leu Pro Pro Pro
             45              50                  55

CCG CCG CCG CCA CCA CTG CCT CCA CTA CCG CTG CCA CCC CTG AAG AAG                304
Pro Pro Pro Pro Pro Leu Pro Pro Leu Pro Leu Pro Pro Leu Lys Lys
             60              65                  70

AGA GGG AAC CAC AGC ACA GGC CTG TGT CTC CTT GTG ATG TTT TTC ATG                352
Arg Gly Asn His Ser Thr Gly Leu Cys Leu Leu Val Met Phe Phe Met
         75              80                  85

GTT CTG GTT GCC TTG GTA GGA TTG GGC CTG GGG ATG TTT CAG CTC TTC                400
Val Leu Val Ala Leu Val Gly Leu Gly Leu Gly Met Phe Gln Leu Phe
 90              95                  100                 105
```

```
CAC  CTA  CAG  AAG  GAG  CTG  GCA  GAA  CTC  CGA  GAG  TCT  ACC  AGC  CAG  ATG      448
His  Leu  Gln  Lys  Glu  Leu  Ala  Glu  Leu  Arg  Glu  Ser  Thr  Ser  Gln  Met
               110                      115                      120

CAC  ACA  GCA  TCA  TCT  TTG  GAG  AAG  CAA  ATA  GGC  CAC  CCC  AGT  CCA  CCC      496
His  Thr  Ala  Ser  Ser  Leu  Glu  Lys  Gln  Ile  Gly  His  Pro  Ser  Pro  Pro
                    125                      130                      135

CCT  GAA  AAA  AAG  GAG  CTG  AGG  AAA  GTG  GCC  CAT  TTA  ACA  GGC  AAG  TCC      544
Pro  Glu  Lys  Lys  Glu  Leu  Arg  Lys  Val  Ala  His  Leu  Thr  Gly  Lys  Ser
               140                      145                      150

AAC  TCA  AGG  TCC  ATG  CCT  CTG  GAA  TGG  GAA  GAC  ACC  TAT  GGA  ATT  GTC      592
Asn  Ser  Arg  Ser  Met  Pro  Leu  Glu  Trp  Glu  Asp  Thr  Tyr  Gly  Ile  Val
          155                      160                      165

CTG  CTT  TCT  GGA  GTG  AAG  TAT  AAG  AAG  GGT  GGC  CTT  GTG  ATC  AAT  GAA      640
Leu  Leu  Ser  Gly  Val  Lys  Tyr  Lys  Lys  Gly  Gly  Leu  Val  Ile  Asn  Glu
170                      175                      180                      185

ACT  GGG  CTG  TAC  TTT  GTA  TAT  TCC  AAA  GTA  TAC  TTC  CGG  GGT  CAA  TCT      688
Thr  Gly  Leu  Tyr  Phe  Val  Tyr  Ser  Lys  Val  Tyr  Phe  Arg  Gly  Gln  Ser
                    190                      195                      200

TGC  AAC  AAC  CTG  CCC  CTG  AGC  CAC  AAG  GTC  TAC  ATG  AGG  AAC  TCT  AAG      736
Cys  Asn  Asn  Leu  Pro  Leu  Ser  His  Lys  Val  Tyr  Met  Arg  Asn  Ser  Lys
               205                      210                      215

TAT  CCC  CAG  GAT  CTG  GTG  ATG  ATG  GAG  GGG  AAG  ATG  ATG  AGC  TAC  TGC      784
Tyr  Pro  Gln  Asp  Leu  Val  Met  Met  Glu  Gly  Lys  Met  Met  Ser  Tyr  Cys
               220                      225                      230

ACT  ACT  GGG  CAG  ATG  TGG  GCC  CGC  AGC  AGC  TAC  CTG  GGG  GCA  GTG  TTC      832
Thr  Thr  Gly  Gln  Met  Trp  Ala  Arg  Ser  Ser  Tyr  Leu  Gly  Ala  Val  Phe
          235                      240                      245

AAT  CTT  ACC  AGT  GCT  GAT  CAT  TTA  TAT  GTC  AAC  GTA  TCT  GAG  CTC  TCT      880
Asn  Leu  Thr  Ser  Ala  Asp  His  Leu  Tyr  Val  Asn  Val  Ser  Glu  Leu  Ser
250                      255                      260                      265

CTG  GTC  AAT  TTT  GAG  GAA  TCT  CAG  ACG  TTT  TTC  GGC  TTA  TAT  AAG  CTC      928
Leu  Val  Asn  Phe  Glu  Glu  Ser  Gln  Thr  Phe  Phe  Gly  Leu  Tyr  Lys  Leu
                    270                      275                      280

TAAGAGAAGC  ACTTTGGGAT  TCTTTCCATT  ATGATTCTTT  GTTACAGGCA  CCGAGAATGT     988

TGTATTCAGT  GAGGGTCTTC  TTACATGCAT  TTGAGGTCAA  GTAAGAAGAC  ATGAACCAAG    1048

TGGACCTTGA  GACCACAGGG  TTCAAAATGT  CTGTAGCTCC  TCAACTCACC  TAATGTTTAT    1108

GAGCCAGACA  AATGGAGGAA  TATGACGGAA  GAACATAGAA  CTCTGGGCTG  CCATGTGAAG    1168

AGGGAGAAGC  ATGAAAAAGC  AGCTACCAGG  TGTTCTACAC  TCATCTTAGT  GCCTGAGAGT    1228

ATTTAGGCAG  ATTGAAAAGG  ACACCTTTTA  ACTCACCTCT  CAAGGTGGGC  CTTGCTACCT    1288

CAAGGGGGAC  TGTCTTTCAG  ATACATGGTT  GTGACCTGAG  GATTTAAGGG  ATGGAAAAGG    1348

AAGACTAGAG  GCTTGCATAA  TAAGCTAAAG  AGGCTGAAAG  AGGCCAATGC  CCCACTGGCA    1408

GCATCTTCAC  TTCTAAATGC  ATATCCTGAG  CCATCGGTGA  AACTAACAGA  TAAGCAAGAG    1468

AGATGTTTTG  GGGACTCATT  TCATTCCTAA  CACAGCATGT  GTATTTCCAG  TGCAATTGTA    1528

GGGGTGTGTG  TGTGTGTGTG  TGTGTGTGTG  TGTGTATGAC  TAAAGAGAGA  ATGTAGATAT    1588

TGTGAAGTAC  ATATTAGGAA  AATATGGGTT  GCATTGGTC   AAGATTTTGA  ATGCTTCCTG    1648

ACAATCAACT  CTAATAGTGC  TTAAAAATCA  TTGATTGTCA  GCTACTAATG  ATGTTTTCCT    1708

ATAATATAAT  AAATATTTAT  GTAGATGTGC  ATTTTTGTGA  AATGAAAACA  TGTAATAAAA    1768

AGTATATGTT  AGGATACAAA  TA                                                1790
```

( 2 ) INFORMATION FOR SEQ ID NO:2:

( i ) SEQUENCE CHARACTERISTICS:
        ( A ) LENGTH: 281 amino acids
        ( B ) TYPE: amino acid -continued (D) TOPOLOGY: linear (ii) MOLECULE TYPE: protein (xi) SEQUENCE DESCRIPTION: SEQ ID NO:2:

```
Met Gln Gln Pro Phe Asn Tyr Pro Tyr Pro Gln Ile Tyr Trp Val Asp
 1               5                  10                  15
Ser Ser Ala Ser Ser Pro Trp Ala Pro Pro Gly Thr Val Leu Pro Cys
             20                  25                  30
Pro Thr Ser Val Pro Arg Arg Pro Gly Gln Arg Arg Pro Pro Pro Pro
             35                  40                  45
Pro Pro Pro Pro Pro Leu Pro Pro Pro Pro Pro Pro Pro Leu Pro
         50                  55                  60
Pro Leu Pro Leu Pro Pro Leu Lys Lys Arg Gly Asn His Ser Thr Gly
 65                  70                  75                  80
Leu Cys Leu Leu Val Met Phe Phe Met Val Leu Val Ala Leu Val Gly
                 85                  90                  95
Leu Gly Leu Gly Met Phe Gln Leu Phe His Leu Gln Lys Glu Leu Ala
            100                 105                 110
Glu Leu Arg Glu Ser Thr Ser Gln Met His Thr Ala Ser Ser Leu Glu
            115                 120                 125
Lys Gln Ile Gly His Pro Ser Pro Pro Pro Glu Lys Lys Glu Leu Arg
            130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
            180                 185                 190
Ser Lys Val Tyr Phe Arg Gly Gln Ser Cys Asn Asn Leu Pro Leu Ser
            195                 200                 205
His Lys Val Tyr Met Arg Asn Ser Lys Tyr Pro Gln Asp Leu Val Met
    210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
            245                 250                 255
Leu Tyr Val Asn Val Ser Glu Leu Ser Leu Val Asn Phe Glu Glu Ser
            260                 265                 270
Gln Thr Phe Phe Gly Leu Tyr Lys Leu
            275                 280
```

FAS LIGAND COMPOSITIONS FOR TREATMENT OF PROLIFERATIVE DISORDERS

FIELD OF THE INVENTION

This invention relates to methods and compositions for the treatment of proliferative disorders, such as the excessive proliferation of vascular smooth muscle cells associated with arteriosclerosis. The methods involve administering a Fas ligand molecule to induce apoptosis in the target cells that are undergoing excessive proliferation.

BACKGROUND OF THE INVENTION

Arteriosclerosis is a disease that is characterized by a thickening and hardening of regions of an arterial wall. A particular type of arteriosclerosis is atherosclerosis, which affects the large arteries and is often the basis for coronary artery disease, aortic aneurysm, arterial disease of the lower extremities, and cerebrovascular disease. Atherosclerosis is characterized by the formation of fibrous plaques that contain a large number of smooth muscle cells, macrophages, collagen, extracellular lipid, and necrotic cell debris. The accumulation of material in a fibrous plaque results in narrowing of the blood vessel lumen which, in turn, restricts arterial blood flow. When the fibrous plaques become sufficiently large to block blood flow completely, the organs that are supplied by the artery undergo ischemia and necrosis. The accumulation of fibrous plaques also weakens the artery, an event which frequently results in rupture of the intima, aneurysm and hemorrhage. Moreover, fragments of the fibrous plaque may detach and form arterial emboli that can precipitate an aortic aneurysm or arterial disease of the lower extremities.

To date, the most frequently used methods for treating atherosclerosis include surgical procedures, drug therapies, and combinations of the foregoing. In general, the drug therapies for treating atherosclerosis are designed to prevent or reduce the accumulation of plaque material. For example, drugs such as diuretics, anti-adrenergic agents, vasodilators, angiotensin-converting enzyme inhibitors, renin inhibitors, and calcium channel antagonists have been used to treat conditions such as hypertension, hyperlipidemia, and hypercholesterolemia, which contribute to the development of atherosclerosis. Surgical methods for treating atherosclerosis include coronary bypass surgery, atherectomy, laser procedures, ultrasonic procedures, and balloon angioplasty. Such methods involve significant risk (e.g., of infection, death) to the patient and, even if successful, fibrous plaque formation frequently occurs at the site of vascular anastomoses, causing reclusion of the surgically-treated vessel.

Balloon angioplasty frequently results in injury to the blood vessel wall. Such vascular injury has been shown to induce proliferation and apoptosis in vascular smooth muscle cells (VSMCs), with the relative amounts of cell proliferation and apoptosis ultimately determining the size of the injury-induced lesion. Although peptide growth factors, receptors and their associated intracellular signaling pathways have been extensively studied in vascular smooth muscle cells (VSMCs), little is known about the VSMC nuclear factors that integrate these signals and initiate the regulatory cascades that determine whether a cell will proliferate, alter its state of differentiation, or undergo apoptosis.

Apoptosis is a cell death pathway that is highly conserved throughout evolution (Ameisen J C, et al., Science 1996; 272:1278–1279). Apoptosis is characterized by membrane blebbing and retention of its integrity, cellular and cytoplasmic shrinkage, and chromosomal fragmentation and condensation, endonuclease activation resulting in the characteristic 180 bp DNA ladder (Yang E and Korsmeyer S J, Blood 1996; 88:386–401). A number of stresses can induce apoptosis in vitro and in vivo, including the administration of glucocorticoids, removal of hormones, chemotherapy, mechanical injury, and DNA damage. Apoptosis is also induced by aberrant cell cycle activity, and can be triggered in cells that express the Fas receptor following activation of the Fas receptor by its natural binding partner, the Fas ligand. Cells expressing the Fas ligand (FasL) bind to cells that express the Fas receptor and thereby initiate a cascade that results in apoptosis (Nagata S and Golstein P, Science 1995; 267:1449–1456).

The Fas ligand is expressed in cytotoxic T lymphocytes and in immune privileged tissues such as the eye and testes. Recently, tumors have been reported to express Fas ligand, presumably, to allow tumor cells to protect themselves from cytotoxic T lymphocytes by inducing apoptosis in these cells (Hahne M et al., Science 1996; 274:1363–1366; Strand S et al., Nature Med. 1996; 2:1361–1366; O'Connell J et al., J. Exp. Med. 1996; 184:1075–1082). Several patents disclose the use of the Fas ligand/Fas receptor system for inducing apoptosis in lymphocytes and, thereby, harnessing the ability of these natural molecules to suppress lymphocyte-mediated immune responses such as autoimmune conditions and tissue rejection. For example, PCT Application no. PCT/US95/06742 ("Use of Fas Ligand to Suppress Lymphocyte-mediated Immune Responses", publication no. WO 95/32627) reports that intact and soluble mouse and human Fas ligand polypeptides and/or genes encoding such polypeptides, may be provided to a recipient mammal to suppress T-lymphocyte-mediated transplant or graft rejection. According to WO 95/32627, the compounds are also effective in suppressing and preventing lymphocyte-mediated primary disease, such as juvenile diabetes, and primary disease re-occurrence by, for example, introducing into a mammal a cell which expresses the Fas ligand.

In view of the foregoing, a need still exists to better understanding the molecular processes underlying injury-induced vascular smooth muscle cell proliferation and apoptosis, and to develop improved drug therapies to replace or supplement the existing methods for treating atherosclerosis and related conditions that are mediated by excessive smooth muscle cell proliferation. Preferably, such drug therapies would be designed to reduce or prevent plaque formation at its earliest stages.

SUMMARY OF THE INVENTION

The invention is based on the discovery that in an animal model of restenosis, transduction of smooth muscle cells with a vector containing a nucleic acid encoding the Fas ligand ("Fas ligand vector") results in a dramatic reduction in lesion formation in vivo. Surprisingly, the dramatic reduction in lesion formation was significantly greater than would have been expected based upon the theoretical numbers of smooth muscle cells transduced with the Fas ligand vector. Although not intending to be bound to a particular theory or mechanism, it is believed that this significantly greater potency is due to the expression of multiple copies of the Fas ligand on the surfaces of the transduced smooth muscle cells. As a result, each Fas ligand-expressing smooth muscle cell becomes a catalyst for the apoptotic cell death of neighboring cells that express the Fas receptor. Cells that are susceptible to Fas ligand-mediated apoptosis include vascular smooth muscle cells (transduced or non-transduced), as well as macrophages and T cells that invade the vessel wall following injury and release growth factors that enhance vascular smooth muscle cell proliferation. Applicant describes herein a newly discovered function for the Fas ligand, namely, the ability to prevent or reduce excessive vascular smooth muscle cell proliferation. Accordingly, the instant invention is directed to compositions and methods that are based upon the discovery of this newly-discovered function.

According to one aspect of the invention, a method for treating a subject diagnosed as having a condition associated with excessive vascular smooth muscle cell proliferation is provided. Exemplary conditions that are characterized by excessive proliferation of smooth muscle cells include: vascular injury which results in smooth muscle cell proliferation (e.g., restenosis following balloon angioplasty), pulmonary vascular remodeling characterized by smooth muscle cell proliferation, and cardiovascular remodeling characterized by smooth muscle cell proliferation. The method involves administering to the subject an isolated Fas ligand molecule (a "Fas ligand nucleic acid" or a "Fas ligand polypeptide") in an amount effective to prevent or reduce excessive vascular smooth muscle cell proliferation in vivo. Preferably, the Fas ligand molecule is administered to the subject in conjunction with a method for treating an arteriosclerotic condition. The method for treating an arteriosclerotic condition may be a surgical method or a drug therapy (e.g., gene therapy). The compositions and methods of the invention are useful for replacing existing drug therapies, as well as for improving the effectiveness of existing therapies for treating conditions that are characterized by excessive vascular smooth muscle cell proliferation. In general, such conditions are diagnosed by detecting the presence of fibrous plaques in the blood vessel walls of the subject.

In the particularly preferred embodiments, the Fas ligand molecule is delivered directly to the site at which there is excessive vascular smooth muscle cell proliferation, i.e., the site of vascular injury. For example, this can be accomplished by attaching a Fas ligand nucleic acid or a Fas ligand polypeptide to the surface of a balloon catheter, inserting the catheter into the subject until the balloon portion is located at the site of an occlusion, and inflating the balloon to contact the balloon surface with the vessel wall at the site of the occlusion. In this manner, the compositions can be targeted to particular sites within a vessel to prevent or reduce smooth muscle cell proliferation at these sites. Optionally, the Fas ligand molecule is delivered in combination with a cytokine that promotes endothelial cell proliferation, or a nucleic acid encoding a cytokine that promotes endothelial cell proliferation.

A "Fas ligand molecule" embraces a "Fas ligand nucleic acid" and a "Fas ligand polypeptide". As used herein, a "Fas ligand nucleic acid" refers to a nucleic acid molecule which: (1) hybridizes under stringent conditions to a nucleic acid having the sequence of SEQ. ID NO.1 (the human Fas ligand molecule) and (2) codes for a Fas ligand polypeptide that prevents or reduces the proliferation of vascular smooth muscle cells. The preferred Fas ligand nucleic acid has the sequence of SEQ. ID NO.1. Homologs and alleles of a nucleic acid having the sequence of SEQ. ID NO.1 also are embraced within the definition of a "Fas ligand nucleic acid". In addition, the Fas ligand nucleic acids of the invention include nucleic acids which code for the Fas ligand polypeptide having the sequence of SEQ. ID NO.2, but which differ from the sequence of SEQ. ID NO.1 in codon sequence due to the degeneracy of the genetic code. The invention also embraces isolated functionally equivalent fragments, variants, and analogs of the foregoing nucleic acids; proteins and peptides coded for by any of the foregoing nucleic acids; and complements of the foregoing nucleic acids. Particularly preferred fragments of the Fas ligand nucleic acid and Fas ligand polypeptides are discussed below.

As used herein, a "Fas ligand polypeptide" refers to a polypeptide that is coded for by a Fas ligand nucleic acid. Fas ligand polypeptides are useful for reducing or preventing excessive vascular smooth muscle cell proliferation. The preferred Fas ligand polypeptide of the invention has the amino acid sequence of SEQ. ID NO.2. Fas ligand polypeptides further embrace functionally equivalent fragments, variants, and analogs of SEQ. ID NO.2, provided that the fragments, variants, and analogs reduce or prevent excessive vascular smooth muscle cell proliferation. The invention also embraces proteins and peptides coded for by any of the foregoing nucleic acids. For example, the invention embraces proteins and polypeptides which are coded for by unique fragments of the foregoing nucleic acids. Such proteins and polypeptides are useful, for example, as immunogens for generating antibodies to unique epitopes of the Fas ligand polypeptide.

According to certain embodiments of the invention, an isolated Fas ligand nucleic acid is administered to a subject in need thereof in an amount effective to prevent or reduce excessive vascular smooth muscle cell proliferation in vivo. The subjects are treated with the Fas ligand nucleic acid in a manner and in an amount so as to reduce excessive smooth muscle cell proliferation at the site of injury while minimizing the potential for systemic toxicity. Further specificity of treatment is achieved by operably coupling the Fas ligand nucleic acid to an inducible promoter or a tissue-specific promoter, such as a smooth muscle cell-specific promoter.

According to yet other embodiments of the invention, an isolated Fas ligand polypeptide is administered to a subject in need thereof in an amount effective to prevent or reduce excessive vascular smooth muscle cell proliferation in vivo. The subjects are treated with the Fas ligand polypeptide in a manner and in an amount so as to reduce excessive smooth muscle cell proliferation at the site of injury while minimizing the potential for systemic toxicity.

The complete coding sequence for a human Fas ligand cDNA and predicted amino acid sequence have been assigned Genbank Accession No. U08137 and are provided herewith as SEQ. ID NOS.1 and 2, respectively. The preferred Fas ligand nucleic acids of the invention encode the Fas ligand polypeptides having the amino acid sequence of SEQ. ID NO.2, homologs and alleles of SEQ. ID NO.2, or functionally equivalent fragments or variants of SEQ. ID NO.2. Preferably, the Fas ligand nucleic acid has the nucleotide sequence of SEQ. ID NO.1, the nucleotide sequence encoding the human "intact Fas ligand polypeptide", i.e., complete coding sequence of the gene encoding the human Fas ligand. The intact human Fas ligand polypeptide contains three domains: a cytoplasmic domain (amino acids 1–80); a transmembrane domain (amino acids 81–102); and an extracellular domain (amino acids 103–281); the numbering is based upon that reported by Tanaka M et al., in EMBO J. 14(6):1129–1135 (1995) for the human Fas ligand.

The isolated nucleic acids of the invention also include nucleic acids encoding fragments of an intact Fas ligand. For example, the Fas ligand nucleic acid may encode a "soluble Fas ligand polypeptide" or a "membrane-associated Fas ligand polypeptide". Soluble Fas ligand polypeptides, nucleic acids encoding same, and vectors containing said nucleic acids are described in Tanaka M et al., EMBO J. 14(6):1129–1135 (1995) and in PCT Application no. PCT/US95/06742 ("Use of Fas Ligand to Suppress Lymphocyte-mediated Immune Responses", publication no. WO 95/32627). The soluble Fas ligand polypeptides lack a transmembrane domain. Administration of the intact and soluble Fas ligand nucleic acids and polypeptides has been proposed for treating lymphocyte-mediated immune disorders, such as those described above. No prior use for the membrane-associated Fas ligand polypeptides disclosed herein has been proposed.

Fas ligand polypeptide fragments that are "membrane-associated Fas ligand polypeptides" contain a transmembrane domain and, at least, the Fas receptor binding domain of an extracellular domain (e.g., amino acids 81–281 of SEQ. ID NO.2) but do not include a cytoplasmic domain (e.g., amino acids 1–80 of SEQ. ID NO.2). Membrane-associated Fas ligand polypeptides previously have not been described. Accordingly, one particular aspect of the invention relates to such membrane-associated Fas ligand polypeptides, nucleic acids encoding same, complements of said nucleic acids, vectors containing said nucleic acids, host cells containing said vectors, antibodies that selectively bind to said polypeptides but that do not bind to the intact or soluble Fas ligand polypeptides, and methods for using the foregoing compositions. The invention further embraces nucleic acid molecules that differ from the foregoing isolated nucleic acid molecules in codon sequence due to the degeneracy of the genetic code.

In the preferred embodiments of the methods, the Fas ligand nucleic acid is selected from the group consisting of an intact Fas ligand nucleic acid (e.g., SEQ. ID NO.1, the coding region of SEQ. ID NO.1), a soluble Fas ligand nucleic acid (e.g., encoding amino acids 103–281 of SEQ. ID NO.2, more preferably, encoding amino acids 127–281 of SEQ. ID NO.2), and a membrane-associated Fas ligand nucleic acid (e.g., encoding amino acids 81–281 of SEQ. ID NO.2) that encodes a functionally equivalent fragment of an intact Fas ligand. The Fas ligand nucleic acid is operatively coupled to a promoter that can express the Fas ligand in a targeted cell (e.g., a vascular smooth muscle cell). Preferably, the nucleic acid is contained in an appropriate expression vector (e.g., adenoviral vector, modified adenoviral vector, retroviral vector, plasmid, liposome) to more efficiently genetically modify the targeted cell and achieve expression of the Fas ligand on the targeted cell surface.

According to one aspect of the invention, a method is provided for treating a subject that has sustained a vascular injury which results in, or is otherwise associated with, smooth muscle cell proliferation. A Fas ligand nucleic acid is administered to a subject in need of such treatment in an amount effective to inhibit vascular smooth muscle cell proliferation resulting from, or associated with, the injury. The Fas ligand nucleic acid preferably is as described above. In one embodiment, the Fas ligand nucleic acid is administered to a subject with an arterial occlusion in conjunction with treatment of that occlusion. The occlusion can be a coronary artery occlusion and the treatment can be dilation balloon angioplasty. Vascular smooth muscle cells ("VSMCs") express the Fas receptor and, accordingly, these cells are susceptible to Fas ligand-mediated apoptosis. In contrast, the endothelial cells of the vessel wall do not express the Fas receptor and are not susceptible to Fas ligand-mediated apoptosis. As a result, delivery of a nucleic acid encoding the Fas ligand to a site of vascular injury creates a local region of sustained VSMC apoptosis without harming the beneficial endothelial cells of the vessel wall.

According to another aspect of the invention, a method for inhibiting pulmonary vascular remodeling in a subject is provided. A Fas ligand nucleic acid is administered to a subject in need of such treatment in an amount effective to inhibit pulmonary vascular remodeling. The preferred Fas ligand nucleic acids are as described above. This method is useful, for example, for treating pulmonary vascular remodeling which results from hypoxia.

According to still another aspect of the invention, a method is provided for treating a subject to inhibit cardiovascular remodeling characterized by smooth muscle cell proliferation. A Fas ligand nucleic acid is administered to a subject in need of such treatment in an amount effective to inhibit smooth muscle cell proliferation associated with the cardiovascular remodeling. The preferred Fas ligand nucleic acids are as described above.

It is to be understood that a Fas ligand polypeptide can be used in place of a Fas ligand nucleic acid in treating any of the foregoing conditions. Thus, according to still another aspect of the invention, pharmaceutical preparations are provided that contain a Fas ligand nucleic acid or a Fas ligand polypeptide. The pharmaceutical preparations contain the above-described Fas ligand molecules, together with a pharmaceutically-acceptable carrier. Preferably, the Fas ligand molecules are present in the compositions in an amount effective for treating restenosis associated with balloon dilation angioplasty, pulmonary hypertension or vascular remodeling. The Fas ligand molecules are particularly useful for the treatment of late vein graft occlusion following bypass surgery. This amount is sufficient to inhibit excessive smooth muscle cell proliferation in vivo.

According to still another aspect of the invention, the above Fas ligand molecules (Fas ligand nucleic acids and Fas ligand polypeptides) are used in the preparation of medicaments, preferably for the treatment of restenosis, pulmonary hypertension, or vascular remodeling. The method involves placing the Fas ligand molecules in a pharmaceutically-acceptable carrier. The preferred Fas ligand molecules are as described above.

It is noted that the preferred subjects treated according to the methods set forth above are otherwise free of symptoms calling for Fas ligand treatment, either by administration of the Fas ligand polypeptide or by a Fas ligand nucleic acid. For example, the Fas ligand, functionally active soluble fragments of the Fas ligand and nucleic acids encoding the Fas ligand and its functionally active fragments have been suggested as immunosuppressive agents for inhibiting lymphocyte-mediated immune responses; accordingly, the preferred subjects are free of symptoms calling for treatment with an immunosuppressive agent and, in particular, are free of symptoms calling for treatment with an agent for suppressing a lymphocyte-mediated immune response. Activated lymphocytes also have been reported to be associated with disease in graft versus host reactions (e.g., bone marrow transplantation, chronic and acute graft rejection), and most forms of autoimmunity, including multiple sclerosis, rheumatoid arthritis, lupus, and myasthenia gravis, and leukemia; accordingly, the preferred subjects are free of the foregoing conditions. The Fas ligand, functionally active soluble portions of the Fas ligand and nucleic acids encoding the foregoing polypeptides also have been suggested for treatment of subjects having lymphocyte-mediated primary disease, such as juvenile diabetes, or re-occurrence of such disease; accordingly, the preferred subjects are free of lymphocyte-mediated primary disease, such as diabetes. As yet another example, the Fas ligand, functionally active soluble portions of the Fas ligand and nucleic acids encoding the foregoing polypeptides have been suggested for providing immune protection for viral vectors and genes used in gene therapies; accordingly, the preferred subjects are not otherwise being treated using a viral vector gene therapy protocol.

The invention also contemplates the use of Fas ligand molecules in experimental model systems to determine the role that smooth muscle cell proliferation plays in the repair of an injury to a vessel wall or in mediating an adverse health consequence occurring as a result of such smooth muscle cell proliferation. An injury to a blood vessel of an animal or a pulmonary hypertensive state is induced experimentally, for example, by scraping the endothelial lining of a vessel at a particular site or by inducing a hypoxic state. A Fas ligand molecule as described above then is administered to the animal. The application may be local or may be systemic. Then the animal's response is monitored and compared to control animals that do not receive the Fas ligand molecules.

These and other aspects of the invention will be described in greater detail below. Throughout this disclosure, all technical and scientific terms have the same meaning as commonly understood by one of ordinary skill in the art to which this invention pertains unless defined otherwise.

DETAILED DESCRIPTION OF THE INVENTION

The invention is based on the discovery that the delivery at the site of a vascular injury of an adenoviral vector containing a nucleic acid encoding the Fas ligand ("FasL") polypeptide results in a local region of sustained apoptotic cell death. Local delivery of the Fas ligand nucleic acid is believed to create a condition that is similar to that found in "immune-privileged" tissues (e.g. eye and testis as well as some tumors) which express FasL and eliminate by apoptosis the Fas-bearing T cells that enter the tissue (French L E, et al., J. Cell. Biol.1996; 133:335–343; Hahne M, et al., Science 1996; 274:1363–1366; Strand S, et al., Nature Med. 1996; 2:1361–1366; O'Connell J, et al., J. Exp. Med. 1996; 184:1075–1082). Accordingly, the compositions of the invention contain Fas ligand molecules (Fas ligand nucleic acids and Fas ligand polypeptides) and methods for delivering these molecules in vivo or in vitro for the purpose of inhibiting the excessive proliferation of cells that express the Fas receptor.

The Fas ligand is a membrane-associated polypeptide that upon binding to a Fas receptor, induces apoptosis in the cell expressing the receptor. In one aspect, the invention involves the use of a nucleic acid encoding the Fas ligand ("Fas ligand nucleic acid") to express one or more copies of the Fas ligand on the surface of a target cell and allowing the target cell to contact one or more Fas receptor-expressing cells. Binding of the Fas ligand to the Fas receptor induces apoptosis in the Fas receptor-expressing cell. Although not intending to be bound by any particular theory or mechanism, it further is believed that infection of the vessel wall with, for example, a Fas ligand containing viral vector, results in a "neighboring cell" effect in that the transduced, Fas ligand-expressing vascular smooth muscle cells ("VSMCs") become catalysts for the apoptotic cell death of surrounding cells that express the Fas receptor, e.g., neighboring VSMCs (infected or uninfected), as well as macrophages and T cells.

The human and mouse Fas ligand genes have been isolated and sequenced (Takahashi et al., Intl. Immunol. 6:1567–1574 (1994); Takahashi et al., Cell 76:969–976 (1994)). See also, Genbank Accession No. U08137 (SEQ. ID NOS.1 and 2) for the human Fas ligand cDNA and predicted amino acid sequences, respectively.

In one aspect, the invention is directed to a method for treating a subject diagnosed as having a condition associated with excessive vascular smooth muscle cell or other excessive cell proliferation. Exemplary conditions that are caused by excessive vascular smooth muscle cell proliferation are known to those of ordinary skill in the art and include, but are not limited to, the following diseases: arteriosclerosis, including atherosclerosis and post interventional restenosis or other vessel wall injury-induced excessive vascular smooth muscle cell proliferation, and vascular remodeling, including pulmonary vascular remodeling and cardio-vascular remodeling that is characterized by excessive smooth muscle cell proliferation. The Fas ligand molecules of the invention are particularly useful for the treatment of late vein graft occlusion following bypass surgery. The method involves administering to the subject an isolated Fas ligand molecule in an amount and in a manner effective to prevent or reduce excessive vascular smooth muscle cell or other cell proliferation in vivo. For the treatment of late vein graft occlusion following bypass surgery, the Fas ligand molecules may, alternatively, be administered by perfusing or soaking the vein graft in a solution containing the vein graft prior to implantation.

The Fas ligand molecules of the invention are administered in effective amounts. An effective amount is a dosage of the Fas ligand nucleic acid sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with restenosis, an effective amount is that amount which slows or inhibits the growth of smooth muscle cells associated with restenosis. Likewise, an effective amount for treating vascular remodeling would be an amount sufficient to lessen or inhibit altogether smooth muscle cell proliferation so as to slow or halt the development of or the progression of vascular remodeling. Thus, it will be understood that the Fas ligand molecules of the invention can be used to treat the above-noted conditions prophylactically in subjects at risk of developing the foregoing conditions. As used in the claims, "inhibit" embraces all of the foregoing. It is preferred generally that a maximum does by used, that is, the highest safe dose according to sound medical judgment.

A particularly important aspect of the invention involves the use of the Fas ligand molecules of the invention for treating subjects who have sustained a vascular injury such as an injury to a blood vessel. Injury to the vascular system can lead to a number of undesirable health conditions, including, for example, forms of atherosclerosis and arteriosclerosis that are associated with excessive vascular smooth muscle cell proliferation. A common injury to the vascular system occurs as a side effect of a medical procedure for treating ischemic heart disease. Ischemia refers to a lack of oxygen due to inadequate perfusion of blood. Ischemia heart disease is characterized by a disturbance in cardiac function due to an inadequate supply of oxygen to the heart. The most common form of this disease involves a reduction in the lumen of coronary arteries, which limits coronary blood-flow.

When ischemic heart disease becomes very serious, management of the disease becomes invasive. Until recently, ischemic heart disease was treated by coronary-artery, bypass surgery. Less invasive procedures, however, now have been developed. These procedures involve the use of catheters introduced into the narrowed region of the blood vessel ("the stenosis") for mechanically disrupting, laser ablating or dilating the stenosis.

The most widely used method to achieve revascularization of a coronary artery is percutaneous transluminal coronary angioplasty. A flexible guide wire is advanced into a coronary artery and positioned across the stenosis. A balloon catheter then is advanced over the guide wire until the balloon is positioned across the stenosis. The balloon then is repeatedly inflated until the stenosis is substantially eliminated. This procedure, as compared to heart surgery, is relatively noninvasive and typically involves a hospital stay of only a few days. The procedure is an important tool in the management of serious heart conditions.

A serious drawback to angioplasty procedures is the re-occurrence of the stenosis at the site of the angioplasty, or "restenosis". The clinical effects of angioplasty include endothelial denudation and vascular wall damage. In many cases, these injuries have been found to cause proliferation of the arterial smooth muscle cells and, it is believed, restenosis. Restenosis may occur in as many as 40% of patients that have undergone an angioplasty procedure. The Fas ligand molecules of the invention can be used to inhibit such excessive smooth muscle cell proliferation. Excessive, with respect to vascular smooth muscle cell or other cell proliferation, refers to an amount of vascular smooth muscle cell proliferation which is (1) greater than the amount of proliferation that occurs in a normal, healthy subject; and (2) results in an adverse medical condition.

The invention also involves the use of the Fas ligand molecules for treating subjects who have primary or secondary pulmonary hypertension. Pulmonary hypertension as used herein means a right ventricular systolic or a pulmonary artery systolic pressure, at rest, of at least 20 mmHg. Pulmonary hypertension is measured using conventional procedures well-known to those of ordinary skill in the art. Pulmonary hypertension can have a variety of etiologies.

The invention also is useful for treating cardiovascular or pulmonary vascular remodeling associated with proliferation of smooth muscle cells and fibroblasts. Cardio-vascular remodeling can arise from numerous conditions, including acute trauma and chronic conditions affecting the cardiovascular system. It can be associated, for example, in connection with corpulmonale, where the pulmonary vasculature as well as portions of the heart undergo changes involving luminal narrowing due to smooth muscle cell proliferation leading to a decreased ejection capacity of the right ventricle because of the greater pressure necessary to push blood though the narrow vessels. Pulmonary vascular remodeling is determined indirectly by echocardiogram or by right heart catheterization assessment of the associated pulmonary hypertension.

A subject, as used herein, refers to any mammal (preferably, a human) that may be susceptible to a condition associated with excessive vascular smooth muscle cell (such as the conditions described above) or other cell proliferation, provided that the mammal is otherwise free of symptoms calling for Fas ligand treatment. The preferred subjects are free of symptoms calling for treatment with an immunosuppressive agent and, in particular, are free of symptoms call for treatment with an agent for suppressing a lymphocyte-mediated immune response. Exemplary conditions that have symptoms calling for treatment with an immunosuppressive agent include: graft versus host reactions (e.g., bone marrow transplantation, chronic and acute graft rejection; most forms of autoimmunity (e.g., multiple sclerosis, rheumatoid arthritis, lupus, and myasthenia gravis, and leukemia); and lymphocyte-mediated primary disease (e.g., juvenile diabetes, adult diabetes), or re-occurrence of such disease. Preferred subjects also are not otherwise being treated using viral vector gene therapy protocols.

A "Fas ligand molecule", as used herein, embraces both "Fas ligand nucleic acids" and "Fas ligand polypeptides" (discussed below). Fas ligand molecules are capable of inducing apoptosis in cells that express a Fas receptor. Accordingly, Fas ligand molecules are capable of reducing or preventing the proliferation of vascular smooth muscle cells in vivo and in vitro by inducing apoptosis in these cells and in neighboring cells that express the Fas receptor.

A "Fas ligand nucleic acid", as used herein, refers to a nucleic acid molecule which: (1) hybridizes under stringent conditions to a nucleic acid having the sequence of SEQ. ID. No.1 and (2) codes for a Fas ligand polypeptide (i.e., a protein which binds to a Fas receptor). Preferably, the Fas ligand polypeptide binds to a Fas receptor on the surface of a Fas receptor-expressing cell and, thereby, induces apoptosis in the Fas receptor-expressing cell. The preferred Fas ligand nucleic acid has the nucleic acid sequence of SEQ. ID No.1. The Fas ligand nucleic acids of the invention also include homologs and alleles of a nucleic acid having the sequence of SEQ. ID. No.1, as well as functionally equivalent fragments, variants, and analogs of the foregoing nucleic acids. "Functionally equivalent", in reference to a Fas ligand nucleic acid fragment, variant, or analog, refers to a nucleic acid that codes for a Fas ligand polypeptide that is capable of binding to a Fas receptor. More specifically, "functionally equivalent" refers to a Fas ligand polypeptide that is capable of binding to a Fas receptor on the surface of a Fas receptor-expressing cell and inducing apoptosis in the Fas receptor-expressing cell (e.g., a vascular smooth muscle cell). In this manner, the Fas ligand molecules of the invention are capable of preventing or reducing excessive smooth muscle cell proliferation in vivo.

The term "isolated", as used herein in reference to a nucleic acid molecule, means a nucleic acid sequence: (i) amplified in vitro by, for example, polymerase chain reaction (PCR); (ii) synthesized by, for example, chemical synthesis; (iii) recombinantly produced by cloning; or (iv) purified, as by cleavage and gel separation. The term "isolated", as used herein in reference to a polypeptide (protein), means a polypeptide encoded by an isolated nucleic acid sequence, as well as polypeptides synthesized by, for example, chemical synthetic methods, and polypeptides separated from biological materials, and then purified using conventional protein analytical procedures.

Preferably, the Fas ligand nucleic acid has the nucleotide sequence of SEQ. ID NO.1, the nucleotide sequence encoding an "intact Fas ligand polypeptide", i.e., the complete coding sequence of the gene encoding the human Fas ligand. The intact human Fas ligand polypeptide contains three domains: a cytoplasmic domain (amino acids 1–80); a transmembrane domain (amino acids 81–102); and an extracellular domain (amino acids 103–281); the numbering is based upon that reported by Tanaka M et al., EMBO J. 14(6):1129–1135 (1995) for the human Fas ligand.

The isolated Fas ligand nucleic acids of the invention also include nucleic acids encoding fragments of an intact Fas ligand. Preferably, the fragments are functional equivalents of the intact Fas ligand nucleic acid. For example, the Fas ligand nucleic acids may encode a fragment that is a "soluble Fas ligand polypeptide" or a fragment that is a "membrane-associated Fas ligand polypeptide". Soluble Fas ligand polypeptides, nucleic acids encoding same, and vectors containing said nucleic acids are described in Tanaka M et al., EMBO J. 14(6):1129–1135 (1995) and in PCT Application No. PCT/US95/06742 ("Use of Fas Ligand to Suppress Lymphocyte-mediated Immune Responses", publication no. WO 95,32627). The soluble Fas ligand polypeptides lack a transmembrane domain. Although administration of the intact and soluble Fas ligand polypeptides has been proposed for treating lymphocyte-mediated immune disorders, the membrane-associated Fas ligand nucleic acids and polypeptides that are fragments of an intact Fas ligand nucleic acid and polypeptide, respectively, previously have not been disclosed.

Fas ligand polypeptide fragments that are "membrane-associated Fas ligand polypeptides" contain a transmembrane domain and, at least, the Fas receptor binding domain of an extracellular domain (e.g., amino acids 81–281 of SEQ. ID NO.2) but do not include a cytoplasmic domain (e.g., amino acids 1–80 of SEQ. ID NO.2). Preferably, the membrane-associated Fas ligand polypeptides contain the transmembrane domain of SEQ. ID NO.2. The Fas ligand polypeptide of SEQ. ID NO.2 is an exemplary Type II transmembrane protein (Tanaka M et al., in EMBO J. 14(6):1129–1135 (1995)). Accordingly, alternative embodiments of these functionally equivalent fragments of the Fas ligand polypeptide contain a transmembrane domain derived from, e.g., another Type II transmembrane protein, coupled to at least the Fas receptor binding domain of the Fas ligand extracellular domain. Membrane-associated Fas ligand polypeptides that are functionally equivalent fragments of an intact Fas ligand previously have not been described. Accordingly, one particular aspect of the invention relates to such membrane-associated Fas ligand polypeptides, nucleic acids encoding same, complements of said nucleic acids, antibodies that selectively bind to said polypeptides and that do not bind to intact or soluble Fas ligand polypeptides, vectors containing said nucleic acids, host cells containing said vectors, and methods for using the foregoing compositions.

The invention also embraces nucleic acid molecules that differ from the foregoing in that the nucleic acids encode a Fas ligand polypeptide that has one or more amino acid substitutions in the cleavage region defined as the amino acid sequence from about amino acid position 117 to about amino acid position 137. The amino acid substitution(s) render the Fas ligand polypeptide incapable of being cleaved in vivo. More preferably, such non-cleavable Fas ligand polypeptides include one or more amino acid substitutions in the region defined by amino acid position 122 to about amino acid position 132. Most preferably, the non-cleavable Fas ligand polypeptides have one or more amino acid substitutions at positions 126, 127 and 128, which render the polypeptide non-cleavable in vivo. For example, the substitution of an amino acid that is not a conservative amino acid substitution (e.g., a basic amino acid substituted for an acidic amino acid, a hydrophobic amino acid substituted for a hydrophilic amino acid) can be used to generate a polypeptide that is incapable of being cleaved in vivo.

In the preferred embodiments of the methods, the Fas ligand nucleic acid is selected from the group consisting of an intact Fas ligand nucleic acid (e.g., SEQ. ID NO.1, the coding region of SEQ. ID NO.1), a soluble Fas ligand nucleic acid (e.g., encoding amino acids 103–281 of SEQ. ID NO.2, more preferably, encoding amino acids 127–281 of SEQ. ID NO.2), and a membrane-associated Fas ligand nucleic acid (e.g., encoding amino acids 81–281 of SEQ. ID NO.2). The Fas ligand nucleic acid is operatively coupled to a promoter that can express the Fas ligand in a targeted cell (e.g., a vascular smooth muscle cell). Preferably, the nucleic acid is contained in an appropriate expression vector (e.g., adenoviral vector, modified adenoviral vector, retroviral vector, plasmid, liposome) to more efficiently genetically modify the targeted cell and achieve expression of multiple copies of the Fas ligand polypeptide on the targeted cell surface.

Fas ligand nucleic acids further embrace nucleic acid molecules which code for the Fas ligand polypeptide having the sequence of SEQ. ID 2 but which differ from the sequence of SEQ. ID NO.1 in codon sequence due to the degeneracy of the genetic code. The invention further embraces unique fragments (which may, or may not be "functional" with respect to encoding a Fas ligand protein) and complements of the foregoing nucleic acids, particularly, unique fragments of the membrane-associated Fas ligand nucleic acids. Such unique fragments can be used, for example, as probes in hybridization assays and as primers in a polymerase chain reaction (PCR) to generate the membrane-associated Fas ligand nucleic acids of the invention.

The Fas ligand nucleic acids of the invention can be identified by conventional techniques, e.g., by identifying nucleic acid sequences which code for Fas ligand polypeptides and which hybridize to a nucleic acid molecule having the sequence of SEQ. ID NO.1 under stringent conditions. The term "stringent conditions", as used herein, refers to parameters with which the art is familiar. More specifically, stringent conditions, as used herein, refer to hybridization at 65° C. in hybridization buffer (3.5×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the Fas ligand nucleic acid of the invention. The skilled artisan also is familiar with the methodology for screening cells and libraries for the expression of molecules, such as Fas ligand, can be isolated, following by isolation of the pertinent nucleic acid molecule and sequencing. In screening for Fas ligand nucleic acid sequences, a Southern blot may be performed using the foregoing conditions, together with a radioactive probe. After washing the membrane to which the DNA is finally transferred, the membrane can be placed against x-ray film to detect the radioactive signal.

In general, homologs and alleles typically will share at least 40% nucleotide identity with SEQ. ID. No.1; in some instances, will share at least 50% nucleotide identity; and in still other instances, will share at least 60% nucleotide identity. Watson-Crick complements of the foregoing nucleic acids are also embraced by the invention. The preferred homologs have at least 70% sequence homology to SEQ. ID. No.1. More preferably the preferred homologs have at least 80% and most preferably at least 90% sequence homology to SEQ. ID. No.1.

The invention also includes degenerate nucleic acids which include alternative codons to those present in the naturally occurring nucleic acid that codes for the human Fas ligand polypeptide. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the naturally occurring isolated nucleic acids in codon sequence due to the degeneracy of the genetic code.

The invention also provides isolated unique fragments of SEQ. ID NO.1 and complements of the foregoing Fas ligand nucleic acids. A unique fragment is one that is a 'signature' for the larger nucleic acid. It, for example, is long enough to assure that its precise sequence is not found in molecules outside of the Fas ligand gene. Unique fragments can be used as probes in Southern blot assays to identify family members or can be used in amplification assays such as those employing PCR. As known to those skilled in the art, large probes such as 200 base pair (BP) or more are preferred for certain uses such as Southern blots, while smaller fragments will be preferred for uses such as PCR. The fragments are also useful as probes for mRNA in Northern blot analysis. Unique fragments also can be used to produce fusion proteins for generating antibodies or for generating immunoassay components. Unique fragments are also useful for a variety of assays to determine the protein binding regions of the nucleic acid, such as gel shift assays and can be cloned into reporter constructs such as a chloramphenicol acetyl transferase (CAT) vector to determine the active promoter and enhancer regions. Likewise, unique fragments can be employed to produce fragments of the Fas ligand polypeptide, such as a membrane-associated Fas ligand polypeptide, useful, for example, in inducing apoptosis in Fas ligand receptor-expressing cells that contact a Fas ligand-expressing cell. Complements of unique fragments further can be used as antisense molecules to inhibit the expression of the Fas ligand polypeptide, particularly for therapeutic purposes as described in greater detail below.

As will be recognized by those skilled in the art, the size of the unique fragment will depend upon its conservancy in the genetic code. Thus, some regions of SEQ. ID. No.1, will require longer segments to be unique while others will require only short segments, typically between 12 and 32 base pairs. Virtually any segment of SEQ. ID NO.1, that is 18 or more nucleotides in length will be unique. Those skilled in the art are well versed in methods for selecting such sequences, typically on the basis of the ability of the unique fragment to selectively distinguish the sequence of interest from other family members. Unique fragments of the membrane-associated Fas ligand polypeptides of the invention, nucleic acids encoding same, are a particularly preferred aspect of the invention. A comparison of the sequence of the fragment to those on known data bases typically is all that is necessary, although in vitro confirmatory hybridization and sequencing analysis optionally is performed.

The Fas ligand nucleic acid, in one embodiment, is operably linked to a gene expression sequence which directs the expression of the Fas ligand nucleic acid within a eukaryotic cell. The "gene expression sequence" is any regulatory nucleotide sequence, such as a promoter sequence or promoter-enhancer combination, which facilitates the efficient transcription and translation of the Fas ligand nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined Fas ligand nucleic acid. The gene expression sequences optionally includes enhancer sequences or upstream activator sequences as desired.

Preferably, the Fas ligand nucleic acid of the invention is linked to a gene expression sequence which permits expression of the Fas ligand nucleic acid in a smooth muscle cell. More preferably, the gene expression sequence permits expression of the Fas ligand nucleic acid in a human vascular smooth muscle cell and does not permit expression of the Fas ligand nucleic acid in hepatocytes and other Fas receptor-expressing cell types because it is undesirable to interfere with the normal proliferation of these cells. A sequence which permits expression of the Fas ligand nucleic acid in a human vascular smooth muscle cell is one which is selectively active in vascular smooth muscle cells and thereby causes the expression of the Fas ligand nucleic acid in these cells. The following promoters can be used to express the Fas ligand nucleic acid in human vascular smooth muscle cells: myosin heavy chain promoter and smooth muscle 22α promoter. Those of ordinary skill in the art will be able to easily identify alternative promoters that are capable of expressing a Fas ligand nucleic acid in a vascular smooth muscle cell.

The Fas ligand nucleic acid sequence and the gene expression sequence are said to be "operably linked" when they are covalently linked in such a way as to place the transcription and/or translation of the Fas ligand coding sequence under the influence or control of the gene expression sequence. If it is desired that the Fas ligand sequence be translated into a functional protein, two DNA sequences are said to be operably linked if induction of a promoter in the 5' gene expression sequence results in the transcription of the Fas ligand sequence and if the nature of the linkage between the two DNA sequences does not (1) result in the introduction of a frame-shift mutation, (2) interfere with the ability of the promoter region to direct the transcription of the Fas ligand sequence, or (3) interfere with the ability of the corresponding RNA transcript to be translated into a protein. Thus, a gene expression sequence would be operably linked to a Fas ligand nucleic acid sequence if the gene expression sequence were capable of effecting transcription of that Fas ligand nucleic acid sequence such that the resulting transcript might be translated into the desired protein or polypeptide.

The Fas ligand nucleic acids of the invention can be delivered to the vascular smooth muscle cell alone or in association with a vector. In its broadest sense, a "vector" is any vehicle capable of facilitating: (1) delivery of a Fas ligand molecule to a target cell and/or (2) uptake of a Fas ligand molecule by a target cell. Preferably, the vectors transport the Fas ligand molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a Fas ligand nucleic acid or a Fas ligand protein) can be selectively delivered to a vascular smooth muscle cell in, e.g., the arterial wall. Methodologies for targeting include conjugates, such as those described in U.S. Pat. No. 5,391,723 to Priest. Another example of a well-known targeting vehicle is a liposome. Liposomes are commercially available from Gibco BRL. Numerous methods are published for making targeted liposomes. Preferably, the Fas ligand molecules of the invention are targeted for delivery to a smooth muscle cell and, more preferably, a vascular smooth muscle cell.

In general, the vectors useful in the invention are divided into two classes: biological vectors and chemical/physical vectors. Biological vectors are useful for delivery/uptake of Fas ligand nucleic acids to/by a target cell. Chemical/physical vectors are useful for delivery/uptake of Fas ligand nucleic acids or Fas ligand proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of biological vector and include, but are not limited to, nucleic acid sequences from the following viruses: adenovirus; adeno-associated virus; retrovirus, such as moloney murine leukemia virus; harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hemopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion. The preparation of an adeno-associated virus containing a nucleic acid encoding the intact human Fas ligand is described in the Examples. This construct is designated "Adeno-FasL" and contains a serotype 5 human replication defective adenovirus encoding the full-length murine Fas ligand cDNA from the CMV promoter/enhancer). Of course, for human subjects, the vector preferably would be constructed by substituting a human Fas ligand nucleic acid for the murine Fas ligand referenced in the working examples.

Adeno-FasL constructs can be constructed by subcloning the FasL cDNA, mouse (Accession #U06948) for human (Accession #U08137), downstream from an appropriate expression cassette (for example, the CMV promoter/enhancer) into the EcoRV site of the pCO1 vector containing the Ad5 adenoviral sequences required for homologous recombination. The resulting plasmid can then be linearized by restriction enzyme digestion and cotransfected in 293 cells with large ClaI fragment of the Ad5 d1324 viral DNA (Stratford-Perricaudet, L. D., et al., 1993, *J. Clin. Invest.* 90:626–630). The resulting replication-defective recombinant adenoviral constructs are then purified from isolated plaques. The viral preparations are typically purified by two CsCl gradient centrifugations, dialyzed against buffer containing 10 mM Tris-Cl pH 7.5, 1 mM $MgCl_2$ and 135 mM NaCl and stored at −80° C. in 10% glycerol. Viral titer is typically determined by plaque assay on 293 cells (Graham, F. L., and A. J. van der Eb, 1973, *Virology* 52:456–463) and expressed as plaque forming units (pfu) per ml.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman C. O., New York (1990) and Murry, E. J. Ed. "Methods in Molecular Biology," vol. 7, Humana Press, Inc., Cliffton, N.J. (1991).

Another preferred retroviral vector is the vector derived from the moloney murine leukemia virus, as described in Nabel, E. G., et al., *Science*, v. 249, p. 1285–1288 (1990). These vectors reportedly were effective for the delivery of genes to all three layers of the arterial wall, including the media, which is composed of smooth muscle cells. Other preferred vectors are disclosed in Flugelman, et al., *Circulation*, v. 85, p. 1110–1117 (1992).

In addition to the biological vectors, chemical/physical vectors may be used to deliver a Fas ligand molecule to a target cell and facilitate uptake thereby. As used herein, a "chemical/physical vector" refers to a natural or synthetic molecule, other than those derived from bacteriological or viral sources, capable of delivering the isolated Fas ligand molecule to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2–4.0μ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the vascular cell wall, by coupling the liposome to a specific ligand such as a monoclonal antibody, sugar, glycolipid, or protein. Ligands which may be useful for targeting a liposome to the vascular wall include, but are not limited to the viral coat protein of the Hemagglutinating virus of Japan. Additionally, the vector may be coupled to a nuclear targeting peptide, which will direct the Fas ligand nucleic acid to the nucleus of the host cell.

Liposomes are commercially available from Gibco BRL, for example, as LIPOFECTIN™ and LIPOFECTACE™, which are formed of cationic lipids such as N-[1-(2,3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235–241 (1985).

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promotor. The polymeric matrix is used to achieve sustained release of the exogenous gene in the patient. In accordance with the instant invention, the Fas ligand nucleic acids described herein are encapsulated or dispersed within the biocompatible, preferably biodegradable polymeric matrix disclosed in PCT/US/03307. The polymeric matrix preferably is in the form of a micro particle such as a micro sphere (wherein the Fas ligand nucleic acid is dispersed throughout a solid polymeric matrix) or a microcapsule (wherein the Fas ligand nucleic acid is stored in the core of a polymeric shell). Other forms of the polymeric matrix for containing the Fas ligand nucleic acid include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver the Fas ligand nucleic acids of the invention to the subject. Biodegradable matrices are preferred. Such polymers may be natural or synthetic polymers. Synthetic polymers arc preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the Fas ligand nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly (butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate). Thus, the invention provides a composition of the above-described Fas ligand molecules for use as a medicament, methods for preparing the medicament and methods for the sustained release of the medicament in vivo. In the preferred embodiments, the Fas ligand nucleic acid has the nucleic acid sequence of SEQ. ID NO.1 or a functionally-equivalent fragment of SEQ. ID NO.1, such as a nucleic acid encoding a soluble Fas ligand polypeptide or a nucleic acid encoding a membrane-associated Fas ligand polypeptide. Preferably, the Fas ligand nucleic acid is operably linked to a gene expression sequence to permit expression of the Fas ligand nucleic acid in the target cell. The preferred Fas ligand protein has the amino acid sequence of SEQ. ID NO.2 or a functionally equivalent fragment of SEQ. ID NO.2 that contains the transmembrane domain and at least the Fas receptor-binding portion of the extracellular domain. The Fas receptor-binding portion of the extracellular domain is determined in receptor binding assays by, for example, proteolytically cleaving the Fas ligand polypeptide and identifying the cleavage fragments that inhibit binding of the intact Fas ligand polypeptide to the Fas receptor. Cleavage fragments that inhibit binding include all or part of the Fas receptor-binding portion of the Fas ligand. In the preferred embodiments, the functionally equivalent fragments of SEQ. ID NO.2 do not contain the cytoplasmic domain.

Compaction agents also can be used alone, or in combination with, a biological or chemical/physical vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the isolated Fas ligand nucleic acid in a form that is more efficiently taken up by the cell or, more preferably, in combination with one or more of the above-described vectors.

Other exemplary compositions that can be used to facilitate uptake by a target cell of the Fas ligand nucleic acids include calcium phosphate and other chemical mediators of intracellular transport, microinjection compositions, electroporation and homologous recombination compositions (e.g., for integrating a Fas ligand nucleic acid into a preselected location within the target cell chromosome).

The Fas ligand nucleic acids code for a Fas ligard polypeptide. As used herein, a "Fas ligand polypeptide" refers to a polypeptide that is coded for by a Fas ligand nucleic acid and that binds to a Fas receptor. Fas ligand polypeptides are useful for reducing or preventing excessive vascular smooth muscle cell proliferation by inducing apoptosis in vascular smooth muscle cells that express the Fas receptor. The preferred Fas ligand polypeptides of the invention has the amino acid sequence of SEQ. ID NO.2 or is a functionally equivalent fragment of SEQ. ID NO.2. Fas ligand polypeptides further embrace functionally equivalent variants, and analogs of SEQ. ID NO.2, provided that the fragments, variants, and analogs bind to a Fas receptor and, thereby, are capable of reducing or preventing vascular smooth muscle cell proliferation. The invention also embraces proteins and peptides coded for by any of the foregoing Fas ligand nucleic acids.

A "functionally equivalent variant" of SEQ. ID NO.2 binds to a Fas receptor and is capable of inducing apoptosis in a vascular smooth muscle cell in vitro or in vivo. An in vitro apoptosis assay (see, e.g., the apoptosis assay provided in the Examples) can be used as a screening assay to measure the ability of a polypeptide to induce apoptosis in a vascular smooth muscle cell in vitro and is predictive of the ability of the polypeptide to induce apoptosis of vascular smooth muscle cells in vivo. Exemplary "functionally equivalent variants" of SEQ. ID. No.2 includes fragments of SEQ. ID. No.2, as well as polypeptide analogs of SEQ. ID. No.2 which contain conservative amino acid substitutions, provided that the polypeptide variants and analogs are capable of binding to a Fas receptor and, thereby, preventing or reducing vascular smooth muscle cell proliferation.

The preferred Fas ligand nucleic acids of the invention encode the Fas ligand having the amino acid sequence of SEQ. ID NO.2, the complete coding sequence of the gene encoding the human Fas ligand. This "intact" human Fas ligand polypeptide contains three domains: a cytoplasmic domain (amino acids 1–80); a transmembrane domain (amino acids 81–102); and an extracellular domain (amino acids 103–281) (Tanaka M et al., EMBO J. 14(6):1129–1135 (1995)).

The invention also embraces compositions containing and methods using "functionally equvialent fragments" of the Fas ligand polypeptide, namely, "soluble Fas ligand polypeptides" and "membrane-associated Fas ligand polypeptides". Preferably, such polypeptides are fragments of SEQ. ID NO.2. Soluble Fas ligand polypeptides, nucleic acids encoding same, and vectors containing said nucleic acids are described in Tanaka M et al., EMBO J. 14(6):1129–1135 (1995) and in PCT Application no. PCT/US95/06742 ("Use of Fas Ligand to Suppress Lymphocyte-mediated Immune Responses", publication no. WO 95/32627). The soluble Fas ligand polypeptides lack a transmembrane domain. Administration of the intact and soluble Fas ligand polypeptides has been proposed for treating lymphocyte-mediated immune disorders. No prior use for the membrane-associated Fas ligand polypeptides disclosed here has been proposed.

Fas ligand polypeptides fragments that are "membrane-associated Fas ligand polypeptides" contain a transmembrane domain and, at least, the Fas receptor binding domain of an extracellular domain (e.g., amino acids 81–281 of SEQ. ID NO.2) but, preferably, do not include a cytoplasmic domain (e.g., amino acids 1–80 of SEQ. ID NO.2). Membrane-associated Fas ligand polypeptides that are functionally equivalent fragments of an intact Fas ligand polypeptide previously have not been described. Accordingly, one particular aspect of the invention relates to such membrane-associated Fas ligand polypeptides, nucleic acids encoding same, complements of said nucleic acids, vectors containing said nucleic acids, host cells containing said vectors, and methods for using the foregoing compositions. Alternative embodiments include Fas ligand polypeptides that are identical in amino acid sequence to SEQ. ID NO.2 and fragments of SEQ. ID NO.2, but which differ from SEQ. ID NO.2 in having one or more amino acid substitutions in the cleavage region defined as the amino acid sequence from about amino acid position 117 to about amino acid position 137. The amino acid substitution is selected to render the Fas ligand polypeptide incapable of being cleaved in vivo (i.e., a "non-cleavable Fas ligand polypeptide"). More preferably, such non-cleavable Fas ligand polypeptides include one or more amino acid substitutions in the region defined by amino acid position 122 to about amino acid position 132. Most preferably, the non-cleavable Fas ligand polypeptides have one or more amino acid substitutions at positions 126, 127 and 128, which render the polypeptide non-cleavable in vivo. For example, the substitution of an amino acid that is not a conservative amino acid substitution (e.g., a basic amino acid substituted for an acidic amino acid, a hydrophobic amino acid substituted for a hydrophilic amino acid) can be used to generate a polypeptide that is incapable of being cleaved in vivo. Genetic modification of a smooth muscle cell in vivo with a Fas ligand nucleic acid encoding such "non-cleavable" Fas ligand polypeptides advantageously maintains the Fas ligand at the smooth muscle cell surface and, thereby, permits the formation of a localized region of induced apoptosis in the vacinity of the genetically modified smooth muscle cell.

It will be appreciated by those skilled in the art that various modifications of the Fas ligand polypeptide having the sequence of SEQ. ID. No.2 or functionally equivalent fragments of SEQ. ID NO.2 can be made without departing from the essential nature of the invention. Accordingly, it is intended that polypeptides which have the amino acid sequence of SEQ. ID NO.2 but which include conservative substitutions are embraced within the instant invention. As used herein, "conservative amino acid substitution" refers to an amino acid substitution which does not alter the relative charge or size characteristics of the polypeptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D. Fusion proteins, in which a peptide of the invention is coupled to a solid support (such as a polymeric bead), a carrier molecule (such as keyhole limpet hemocyanin), or a reporter group (such as radiolabel or other tag), also are embraced within the invention.

When used therapeutically, the isolated Fas ligand molecules of the invention are administered in therapeutically effective amounts. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg//kg to about 20 mg/kg, in one or more dose administrations daily, for one or more days.

The therapeutically effective amount of the isolated Fas ligand molecule is that amount effective to inhibit excessive proliferation in a vascular smooth muscle or other cell as determined by, for example, standard tests known in the art. It is believed that the Fas ligand molecules inhibit excessive proliferation in the target cells by inducing apoptosis in Fas receptor-expressing cells that are in the vicinity of the target cell. For example, TUNEL staining, and the appearance of condensed chromatin and other morphological features characteristic of apoptosis in electron micrographs can be used to assess apoptosis in vascular smooth muscle and other cell types.

Optionally, the isolated Fas ligand molecule is administered to the subject in combination with a method for treating an arteriosclerotic condition. An arteriosclerotic condition, as used herein, is a term of art that refers to classical atherosclerosis, accelerated atherosclerosis, atherosclerotic lesions and other physiological conditions characterized by undesirable vascular smooth muscle cell proliferation. See, e.g., Harrisons, Principles of Internal Medicine (McGraw Hill, Inc., New York) for a more detailed description of these conditions. The method for treating an arteriosclerotic condition may be a surgical method, an agent for treating restenosis, a method involving a drug therapy (e.g., gene therapy) or a combination of the foregoing.

Surgical methods for treating an arteriosclerotic condition include procedures such as bypass surgery, atherectomy, laser procedures, ultrasonic procedures, and balloon angioplasty.

In a preferred embodiment of the invention, the isolated Fas ligand molecule is administered to a subject in combination with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the arterial wall. As a result, the layer of endothelial cells on the surface of the artery is disrupted, thereby exposing the underlying vascular smooth muscle cells. The isolated Fas ligand molecule is attached to the balloon angioplasty catheter in a manner which permits release of the isolated Fas ligand molecule at the site of the atherosclerotic plaque. The isolated Fas ligand molecule may be attached to the balloon angioplasty catheter in accordance with standard procedures known in the art. For example, the isolated Fas ligand molecule may be stored in a compartment of the balloon angioplasty catheter until the balloon is inflated, at which point it is released into the local environment. Alteratively, the isolated Fas ligand molecule may be impregnated on the balloon surface, such that it contacts the cells of the arterial wall as the balloon is inflated. The Fas ligand molecule also may be delivered in a perforated balloon catheter such as those disclosed in Flugelman, et al., *Circulation*, v. 85, p. 1110–1117 (1992). See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid or polypeptide to the balloon angioplasty catheter.

Additionally, the Fas ligand molecule may be administered with an agent for treating or preventing clinically significant restenosis, which often occurs following balloon angioplasty procedures. Restenosis is narrowing of the artery which occurs in 25% to 50% of patients within 6 months of an angioplasty procedure. Although restentosis was originally believed to be due completely to local tissue growth, recent findings have suggested that it may be due to a combination of tissue growth and vessel constriction. Moreover, although intravascular stents are being widely used to prevent vessel constriction, such stents induce tissue growth and, thereby, promote restenosis. Accordingly, the delivery of an anti-proliferative, such as the Fas ligand molecules of the invention, is believed to be useful for treating vascular remodeling, in general, and in-stent restenosis, in particular.

A preferred agent for preventing restenosis, in combination with the Fas ligand molecule, is a stent. Stents are discussed in a review article by Topol, E. J., the contents of which are hereby incorporated by reference (Topol, E. J., N. E. J. Med. 331: 539–41 (1994)). Stents include, for example, the Gianturco-Roubin stent and the Palmaz-Schatz stent.

The arteriosclerotic conditions also can be treated by a nonsurgical method such as a drug therapy. Many drugs have been used to treat various aspects of an arteriosclerotic condition. For example, drugs have been used to treat physiological extents, such as hypertension and excessive cholesterol accumulation, which are believed to contribute to the formation of atherosclerotic plaques. Other drugs influence the site of injury by breaking up or reducing the size of atherosclerotic plaques, and/or increasing the strength of the arterial wall. The isolated Fas ligand molecule may be administered in conjunction with either or a combination of drugs which inhibit the physiological events contributing to arteriosclerosis or drugs which function directly to reduce the local site of injury associated with atherosclerosis.

Drug therapies which have been found to be useful in treating the physiological events contributing to the development of the atherosclerotic injury, include, but are not limited to, the following drugs: diuretics, antiadrenergic agents, vasodilators, calcium channel antagonists, angiotensin-converting enzyme (ACE) inhibitors, angiotensin II antagonists, and clot dissolvers.

Diuretics include thiazides, e.g., hydrochlorothiazide; loop acting diuretics, e.g., furosemide; potassium-sparing, e.g., spironolactone, triamterene, and amiloride.

Antiadrenergic agents include clonidine; guanabenz; guanfacine; methyldopa; trimethapajn; Rauwolfia alkaloids, e.g., reserpine; guanethidine; guanadrel; phentolamine; phenoxybenzamine; prazosin; terazosin; propranolol; metoprolol; nadolol; atenolol; timolol; timdolol; acebutolol; and labetalol.

Vazodilators include hydralazine; minoxidil; diazoxide; and nitroprusside.

Calcium channel antagonists include nisadipine; diltiazen; and verapamil.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin -(1–8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1–7 (1988)); 4,5,6,7-tetrahydro-1H-imidazo [4, 5-c] pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1, 3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); A$_2$ agonists (Marion Merrill Dow) and certain non-peptide heterocycles (G. D. Searle and Company).

ACE, is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE, thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Drugs which are clot dissolvers include thrombolytic agents which have been used in the treatment of acute venous thromboembolism and pulmonary emboli and are well known in the art (e.g. see Hennekens et al, J Am Coll

*Cardiol*; v. 25 (7 supp), p. 18S–22S (1995); Holmes, et al, *J Am Coll Cardiol*; v. 25 (7 suppl), p. 10S–17S(1995)). Thrombolytic agents include, for example, direct acting agents such as streptokinase and urokinase, and second generation agents such as tissue plasminogen activator (tPA).

Drug therapies which influence the site of injury include any drug which contributes to the reduction of an atherosclerotic plaque or to the strengthening of the arterial wall in the local area of injury. Drugs which help to contribute to the reduction of the plaque include cytostatic molecules and antisense agents to cell cycle regulatory molecules. Other drugs which contribute to the strengthening of the arterial wall include drugs which promote endothelial cell proliferation and function, such as cytokines.

In an embodiment of the invention, the isolated Fas ligand molecule is administered to a subject in combination with a cytostatic molecule. The cytostatic molecule is an agent (e.g., a nucleic acid, a protein) that suppresses cell growth and/or proliferation. A preferred cytostatic molecule is one which inhibits the growth and/or proliferation of vascular smooth muscle cells and includes the growth arrest homeobox molecule (GAX). The GAX molecule is described in published PCT Application WO95/23161. Another preferred cytostatic molecule is GATA-6 (preferably human GATA-6 as described in E. Suzuki, et al., 1996, *Genomics* 38:283–290). Other cytostatic molecules that are active with respect to vascular smooth muscle cells include the retinoblastoma protein (pRB), and cyclic kinase inhibitors, such as p21 and NO donors (Mooradian et al., *J. Cardiovasc. Pharmacol.* 25: 674–8 (1995)).

In another embodiment of the invention, the isolated Fas ligand molecule may be administered to a subject in combination with an antisense oligonucleotide that selectively hybridizes to cell cycle regulatory molecules, such as c-myb, cdc2, cdk2, PCNA, and c-myc under physiological conditions. Such antisense oligonucleotides can function as cytostatic or cytotoxic agent, depending upon the relative amounts of the antisense oligonucleotides that are delivered to the cell and the importance of the particularly targeted cell cycle regulatory molecule to cell growth, proliferation and survival.

Certain cytokines function to strengthen the arterial wall by promoting endothelial cell proliferation. Cytokines which promote endothelial cell proliferation include, but are not limited, to the following: vascular endothelial growth factor (VEGF), basic fibroblast growth factor (bFGF), and acidic fibroblast growth factor (aFGF). Substances that stimulate the proliferation or migration of normal endothelial cells include factors which are associated with the vascularization of tumors and substances which inhibit angiogenesis. Such substances include transforming growth factor beta (TGFβ), tumor necrosis factor alpha (TNFα), human platelet factor 4 (PF4), and alpha interferon (αINF); factors which suppress cell migration, such as proteinase inhibitors, tissue inhibitors of metalloproteinase (TIMP-1 and TIMP-2); and other proteins such as protamine which has demonstrated angiostatic properties.

The above-described drug therapies are well known to those of ordinary skill in the art and are administered by modes know to those of skill in the art. The drug therapies are administered in amounts which are effective to achieve the physiological goals (to prevent or reduce the physiological consequences of atherosclerosis), in combination with the isolated Fas ligand molecule of the invention. Thus, it is contemplated that the drug therapies may be administered in amounts which are not capable of preventing or reducing the physiological consequences of atherosclerosis when the drug therapies are administered alone but which are capable of preventing or reducing the physiological consequences of atherosclerosis when administered in combination with the isolated Fas ligand molecules of the invention.

The isolated Fas ligand molecule may be administered alone or in combination with the above-described drug therapies as part of a pharmaceutical composition. Such a pharmaceutical composition may include the isolated Fas ligand molecule in combination with any standard physiologically and/or pharmaceutically acceptable carriers which are known in the art. The compositions should be sterile and contain a therapeutically effective amount of the isolated Fas ligand molecule in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the Fas ligand molecules, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the Fas ligand molecules into association with a carrier which constitutes one or more accessory ingredients. In general, the compositions are prepared by uniformly and intimately bringing the Fas ligand molecules into association with a liquid carrier, a finely divided solid carrier, or both, and then, if necessary, shaping the product.

Compositions suitable for oral administration may be presented as discrete units, such as capsules, tablets, lozenges, each containing a predetermined amount of the Fas ligand molecule. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the fas ligand molecules described above, increasing convenience to the subject and the physician. Many types of release delivery systems are available and known to those of ordinary skill in the art. They include the above-described polymeric systems, as well as polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the fas ligand molecule is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The isolated Fas ligand molecule may be administered alone or in combination with the above-described drug therapies by any conventional route, including injection or by gradual infusion over time. The administration may, for example, be oral, intravenous, intraperitoneal, intramuscular, intra-cavity, subcutaneous, or transdermal. When using the isolated Fas ligand molecule of the invention, direct administration to the vessel injury site, such as by administration in conjunction with a balloon angioplasty catheter, is preferred.

Preparations for parenteral administration include sterile aqueous or non-aqueous solutions. suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In general, the Fas ligand nucleic acids can be administered to the subject (any mammalian recipient) using the same modes of administration that currently are used for gene therapy in humans (e.g., adenovirus-mediated gene therapy). Preferably, the Fas ligand nucleic acid (contained in, or associated with, an appropriate vector) is administered to the mammalian recipient by balloon angioplasty catheter (described above) or intra-vascular injection. A procedure for performing in vivo gene therapy for delivering a nucleic acid encoding an intact Fas ligand to cells in vivo for treating lymphocyte-mediated immune system disorders is reported in PCT Application no. PCT/US95/06742 ("Use of Fas Ligand to Suppress Lymphocyte-medicated Immune Responses", publication no. WO 95/32627). This publication reports that intact and soluble mouse and human Fas ligand polypeptides and/or genes encoding such polypeptides, may be provided to a recipient mammal to suppress T-lymphocyte-mediated transplant or graft rejection. Alternatively, a patented procedure for performing ex vivo gene therapy is outlined in U.S. Pat. No. 5,399,346 and in exhibits submitted in the file history of that patent, all of which are publicly available documents. In general, ex vivo gene therapy involves introduction in vitro of a functional copy of a gene or fragment thereof into a cell(s) of a subject and returning the genetically engineered cell(s) to the subject. The functional copy of the gene or fragment thereof is under operable control of regulatory elements which permit expression of the gene in the genetically engineered cell(s). Accordingly, the Fas ligand nucleic acids of the invention can be delivered to vascular smooth muscle cells, ex vivo or in vivo, to treat excessive vascular smooth muscle cell proliferation. Because the endothelial cells of the vessel wall do not express the Fas receptor, the transduced smooth muscle cells do not induce Fas ligand-mediated apoptosis in these neighboring endothelial cells; however, the Fas ligand expressed on the surface of the transduced smooth muscle cells mediate apoptosis in the smooth muscle cells that are present in the vicinity of the transduced smooth muscle cells. Numerous transfection and transduction techniques as well as appropriate expression vectors are well known to those of ordinary skill in the art, some of which are described in PCT application WO95/00654.

As an illustrative example, a vector containing a Fas ligand nucleic acid is delivered to a site of vascular injury in a subject who is a candidate for such gene therapy. Then, the vector genetically modifies the vascular smooth muscle cells in vivo with DNA (RNA) encoding a Fas ligand polypeptide of the invention. Such genetically modified vascular smooth muscle cells are expected to inhibit excessive vascular smooth muscle cell proliferation in vivo. In an alternative embodiment, primary human vascular smooth muscle cells can be obtained from a subject who is a candidate for such gene therapy. Then, such cells can be genetically engineered ex vivo with DNA (RNA) encoding a Fas ligand polypeptide of the invention. Such recombinant cells are expected to inhibit vascular smooth muscle cell proliferation in vivo.

Another aspect of the invention includes a screening assay method for determining whether a putative therapeutic agent modulates excessive vascular smooth muscle cell proliferation. The method involves determining the amount of a Fas ligand molecule in a proliferating "test" cell that has been contacted with the putative therapeutic agent to determine whether the putative therapeutic agent modulates cellular proliferation by up or down regulating the amount of the Fas ligand molecule. An increase in the amount of the Fas ligand molecule in the "test" cell indicates that the putative therapeutic agent inhibits cell (e.g. vascular smooth muscle cell) proliferation. Optionally, the level of Fas ligand may be measured in a cell of the same cell type as a negative control in the measurement of proliferation or the level of Fas ligand may be measured in a cell of the same cell type which has been treated with the Fas ligand molecule of SEQ. ID. No.1 or 2 as a positive control in the measurement of proliferation. In one embodiment of the invention the method also involves the step of contacting the Fas ligand molecule with a detection reagent that selectively binds to the Fas ligand molecule to detect or measure the amount of the Fas ligand molecule in the "test" cell. The Fas ligand molecule may optionally be isolated from the vascular smooth muscle or other cell prior to contacting the isolated Fas ligand molecule with the detection reagent. When the Fas ligand molecule is a Fas ligand mRNA, the detection reagent can be a nucleic acid that selectively hybridizes to the Fas ligand mRNA. According to this embodiment, the "test" cell is contacted with the detection reagent under conditions that permit selective hybridization of the nucleic acid to the Fas ligand mRNA. The preferred nucleic acid for this embodiment is a nucleic acid sequence having SEQ. ID. No.1 or a functionally equivalent fragment thereof. Alternatively, the Fas ligand molecule that is being assayed can be a Fas ligand polypeptide and the detection reagent can be an antibody that selectively binds to the Fas ligand protein. The Fas ligand polypeptide can be contacted with the detection reagent under conditions Lhat permit selective binding of a Fas ligand antibody to the Fas ligand polypeptide.

Alternatively, the Fas ligand nucleic acid of the invention can be used to prepare a non-human transgenic animal that can be used, for example, as an animal model (e.g., a Fas ligand knockout animal) of excessive smooth muscle cell proliferation. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of Fas ligand knockout and transgenic animals as models for the study of disorders of vascular blood vessels, such as arteriosclerosis as well as for the study of abnormal cell proliferation associated with tumor growth and metastasis.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division. See e.g., Brinster et al., *Proc. Nat. Acad. Sci. USA*, 82:4438 (1985); Brinster et al., cell 27:223 (1981); Costantini et al., *Nature* 294:982 (1981); Harpers et al., *Nature* 293:540 (1981); Wagner et al., *Proc. Nat. Acad. Sci. USA* 78: 5016 (1981); Gordon et al., *Proc. Nat. Acad. Sci. USA* 73: 1260 (1976). The fertilized egg is then implanted into the uterus of the recipient female and allowed to develop into an animal.

An alternative method for producing transgenic animals involves the incorporation of the desired gene sequence into a virus which is capable of affecting the cells of a host animal. See e.g., Elbrecht et al., Molec. Cell. Biol. 7: 1276 (1987); Lacey et al., Nature 322: 609 (1986); Leopol et al., Cell 51: 885 (1987). Embryos can be infected with viruses, especially retroviruses, modified to carry the nucleotide sequences of the invention which encode Fas ligand proteins or sequences which disrupt the native Fas ligand gene to produce a knockout animal.

Another method for producing transgenic animals involves the injection of pluripotent embryonic stem cells into a blastocyst of a developing embryo. Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. See e.g., Robertson et al., Cold Spring Harbor Conference Cell Proliferation 10: 647 (1983); Bradley et al., Nature 309: 255 (1984); Wagner et al., Cold Spring Harbor Symposium Quantitative Biology 50: 691 (1985).

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47: 897–905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell*, 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, Teratocarcinomas and Embryonic Stem Cells, A Practical Approach, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science*, 244: 1288–1292 (1989). Methods for positive selection of the recombination event (e.g., neo resistance) and dual positive-negative selection (e.g., neo resistance and gangcyclovir resistance) and the subsequent identification of the desired clones by PCR have been described by Capecchi, supra and Joyner et al., *Nature*, 338: 153–156 (1989). The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others. See Houdebine and Chourrout, supra; Pursel et al., *Science* 244: 1281–1288 (1989); and Simms et al., *Bio/Technology*, 6: 179–183 (1988).

Inactivation or replacement of the endogenous Fas ligand gene can be achieved by a homologous recombination system using embryonic stem cells. The resultant transgenic non-human mammals having a knockout Fas ligand characteristic may be used as a model for atherosclerosis. Vascular smooth muscle cells which do not express Fas ligand may be predisposed to proliferate and thus, produce an atherosclerotic phenotype. A variety of therapeutic drugs can be administered to the phenotypically atherosclerotic animals to determine the affect of the therapeutic drugs on vascular smooth muscle cell proliferation. In this manner, therapeutic drugs which are useful for preventing or reducing vascular smooth muscle cell proliferation can be identified. Such agents are useful for, e.g., treating atherosclerosis.

Additionally, a normal or mutant version of Fas ligand can be inserted into the mouse germ line to produce transgenic animals which constitutively or inducible express the normal or mutant form of Fas ligand. These animals are useful in studies to define the role and function of Fas ligand in cells.

The invention will be more fully understood by reference to the following examples. These examples, however, are merely intended to illustrate the embodiments of the invention and are not to be construed to limit the scope of the invention.

EXAMPLES

Introduction to the Examples

Vascular injury has been shown to induce proliferation and apoptosis in vascular smooth muscle cells (VSMCs), and this balance between cell growth and death will ultimately influence the size of the injury-induced lesion. Apoptotic cell death has been documented in human atherectomy and endarterectomy specimens and in a number of animal models of vessel wall stenosis. Recently, we have shown that as early as 30 minutes following balloon injury VSMCs of rat carotid and rabbit iliac arteries undergo apoptotic cell death at a high frequency as demonstrated by TUNEL staining, and by the appearance of condensed chromatin and other morphological features characteristic of apoptosis in electron micrographs. This induction of apoptosis coincides with a marked downregulation of the bcl-X protein, a potential cell death antagonist. Our data suggest that VSMC apoptosis is a rapid and prominent cellular response to acute vascular injury, and the extent of this apoptotic response may ultimately influence characteristics of the lesion that result from the insult. The following Examples include experimental results that evidence the role played by the Fas ligand in the regulation and role of apoptosis in vessel wall lesion formation.

Example 1.

Determine the frequencies of VSMC apoptosis in single-injury and double-injury models of angioplasty in rabbit external iliac arteries.

These experiments examine the relationship between balloon oversize and the frequency of apoptosis and cell loss in normal vessels. Experiments in double-injury hypercholesterolemic rabbits are performed to determine whether neointimal and medial VSMCs differ in their susceptibility to this mechanical/stretch-induced apoptosis. Apoptosis is characterized by both biochemical and morphological criteria, and arterial sections are subjected to immunohistochemical analyses to detect changes in the expression patterns of apoptosis regulatory proteins.

In this Example, the early onset apoptosis in two rabbit models of balloon injury is examined. Experiments in the rabbit model offer a number of advantages: (1) vessels are larger than in the rat, permitting angiographic measurements and the use of angioplasty balloons, (2) normal and hypercholesterolemic animals can be compared, and (3) the rabbit model is more amenable to double-injury experiments permitting an analysis of the effects of balloon injury on the viability of medial versus neointimal VSMCs.

In the first part of this experiment, apoptosis and cell loss as a function of balloon size relative to lumen diameter (determined angiographically) in normal rabbit arteries immediately following injury is examined. Specifically, medial VSMC apoptosis at early time points following injury is determined and the hypothesis that the extent of apoptosis and cell loss is a function of the extent of balloon overstretch is expected to be proven.

In the second part of this experiment, the acute effects of balloon injury on VSMC viability in double injury model in hypercholesterolemic rabbits is examined. Similar to the first part of the study, apoptosis is examined by several methods and cell loss is assessed as a function of balloon size. These experiments allow us to assess whether medial and neointimal VSMCs differ in their susceptibility to barotrauma-induced death. It is anticipated that the double injury model in rabbit will reveal that neointimal and medial VSMCs differ in their sensitivity to mechanical/stretch-induced apoptosis. We believe that these differences in viability are regulated by the differential expression of bcl-2 family proteins in the VSMCs of the media versus the neointima.

Example 1 Materials and Methods:

Several of the procedures that are used to assess apoptosis and cell loss previously have been published. The following materials and methods are taken from Perlman H, et al., Circulation, 1997, 95:981–987.

Rat and rabbit models of arterial lesion formation: The rat carotid model of balloon injury employed in this study was based on that of Clowes et al. (Clowes A W, et al., Lab. Invest. 1983; 49:208–215; Clowes A W, et al., Lab. Invest. 1983; 49:327–333). Male Sprague Dawley rats (n=4 for each time point) were anesthetized with an intraperitoneal injection of sodium pentobarbital (45 mg/kg, Abbot Laboratories). In anesthetized rats the neck area was prepared aseptically, and the bifurcation of the left common carotid artery was exposed through a ventral midline incision. A 2-French Fogarty embolectomy catheter (Baxter Edwards Healthcare Corp.) was introduced into the external carotid artery and advanced to the distal ligation of the common carotid. The balloon was inflated with saline, drawn towards the arteriotomy site and pulled back 3 times to denude the endothelium. The arteriotomy was tied off with a 2.0 silk suture and the subcutis was closed with a 3.0 silk suture. Antibiotics (0.1 ml Di-trim, s.c.) were given immediately post-operatively. Rats were sacrificed at various times following surgery (0 hr, 0.5 hr, 1 hr, 2 hr, 4 hr, 8 hrs post-injury). The injured left and uninjured right common carotid were immediately excised and divided into two populations one was fixed in 4% paraformaldehyde while the other was fixed in methanol. Arterial segments were then embedded in paraffin, cut into longitudinal (5 $\mu$m) sections and assessed by TUNEL labeling and Hoescht 33258 staining. Nuclear density was calculated in multiple sections by counting the number of nuclei per area on a slide stained with hematoxylin and eosin. To provide a positive control for TUNEL labeling, male rats were surgically castrated and sacrificed 3 days post-castration. The ventral prostates were harvested and immediately placed in liquid nitrogen. Frozen sections (5 $\mu$m) were cut and analyzed by TUNEL labeling.

For the rabbit model of balloon angioplasty (n=4) a 20 mm long chalnel balloon angioplasty catheter (Mansfield Medical, Boston Scientific Corp) was introduced through the right carotid artery over a 0.014 inch guide-wire under fluoroscopic guidance and advanced into the abdominal aorta. A baseline angiogram was performed following a single intra-arterial bolus of 200 mg isosrbide dimtrate after interposition of a calibrated grid for computation of the enlargement factor. The balloon angioplasty catheter was advanced into the external iliac artery and then inflated 3 times for one minute periods at a nominal pressure of 6 atm. The balloon was deflated for one minute between each inflation. The size of the balloon was chosen to achieve a 1.4–1.5:1.0 balloon/artery ratio. The non-injured, contralateral iliac artery was used as a control. The animals were sacrificed with a pentobarbital overdose at 30 minutes or 4 hours after the balloon angioplasty procedure. 30 sections of iliac arteries were removed, washed in PBS and immersion fixed in a 4% solution of paraformaldehyde. Arterial segments were then embedded in paraffin, cut into longitudinal sections and assessed. 5 $\mu$m tissue sections were also stained with hematoxylin and eosin following deparafinization and rehydration for conventional light microscopic analysis.

The animal protocols utilized in this study were approved by the Institutional Animal Care and Use Committee of St. Elizabeth's Medical Center, and they complied with the "Guide for the Care and Use of Laboratory Animals" (National Institutes of Health Publication 86-23, revised 1985).

TUNEL Labeling and Nuclear Condensation: The 4% paraformaldehyde fixed sections (5 $\mu$m) were deparafinized and rehydrated. The tissue was permeabilized with 20 mg/ml of proteinase K for 30 minutes. TdT enzyme and dUTP conjugated to a fluorescein cocktail were added to the tissue sections according to the manufacturer's specifications (Boehringer Mannheim in-situ death detection kit). Nuclei were counterstained with Hoescht 33258 (Sigma), and mounted for examination using mounting media for fluorescence (Kirkegaard & Perry Laboratories, Inc.). Specimens were examined and photographed on a Diaphot microscope (Nikon Inc.) equipped with a phase-contrast and epifluorescence optics (×100) lens. Pictures were recorded on Kodak Gold Plus film (Eastman Kodak Co.). The percentage of apoptotic nuclei were calculated by determining the number of Hoechst stained nuclei that were positive for TUNEL staining (N=4 arteries per time point). Approximately 100 nuclei were counted for each section.

Transmission Electron Microscopy: Rat and rabbit uninjured arteries, 30 minutes post-injury and 4 hours post-injury, were excised and fixed in 2.5% glutaraldehyde, 4% paraformaldehyde and 0.1M sodium cacodylate. Sections were post fixed in 1% osmium tetroxide, dehydrated, enbloc stained with 3% uranyl acetate and Sato lead stain and embedded in Epon 812. Thin sections were examined with a Philips CM-10 electron microscope.

Immunohistochemistry: Five micron sections from uninjured and injured rat arterial tissue fixed in methanol were deparafinized and blocked in 10% goat serum. Sections were incubated with rabbit polyclonal anti-bcl-X antibody (Santa Cruz) or rabbit polyclonal anti-bax antibody. Peptide competitions were performed on each section using control peptides at 10 times the concentration of the antibody. Prostates from 3 day castrated rats were used as a positive control. Sections were then washed and incubated with biotinylated goat anti-rabbit antibody. Streptavidin conjugated to alkaline phosphatase was then added to the sections. Signals were determined following the addition of fast red substrate. Sections were counterstained with hematoxylin to visualize nuclei.

Statistical analysis—standard error: All results are expressed as mean±standard error (m±SE). Statistical significance was evaluated using a two tails unpaired Student's t test for comparisons between the means of two groups. A value of $p<0.05$ was interpreted to denote statistical significance.

Example 1 Experimental design:

a) Single-injury model: Approximately 20 normal-fed New Zealand White male rabbits weighing approximately 4.5 kgs are used to evaluate the effect of angioplasty on normal arteries (single injury model). In each animal the angiographic luminal diameter of the iliac artery is determined prior to injury using an automated edge-detection system (LeFree H T, et al., Proc SPIE, 1986; 626:334–341; Mancini G B J, et al., Circulation 1987; 75:452–460). Briefly, a 5 Fr. introducer sheath is positioned in the carotid artery under surgical exposure, and a reference angiogram is obtained following the administration of 0.20 mg nitroglycerin. Then, a channel balloon catheter (Boston Scientific) is advanced over a 0.014" guidewire and is used to perform the balloon injury (3 inflations for 1 minute each at 6 atmospheres with a 1 minute interval between inflations). A channel balloon was chosen for these experiments because it can also be used for subsequent arterial gene transfer experiments (see below).

In this model both iliac arteries are injured with different sizes of channel balloons. Arteries are randomly assigned to receive either a 2.5 mm or a 3.0 mm balloon. Thus the consequences of different balloon-to-artery ratios can be assessed between vessels within the same animal as well as between all of the animals within the experimental group. In preliminary experiments we have found that reference lumen diameters range from 2.00 to 2.50 mm (thus the balloon-to-artery ratio will vary from 1.0 to 1.5). Animals are sacrificed at various times following balloon inflation to assess VSMC apoptosis. These time points include control, 30 minutes, 4 hours, and 3 days post-injury (approximately 5 animals per time point). Injured and uninjured control vessels are excised and portions are fixed in 4% paraformaldehyde for TUNEL analysis, in methanol for immunohistochemical analyses, or in 2.5% glutaraldehyde, 4% paraformaldehyde and 0.1M sodium cacodylate for transmission electron microscopy.

Analyses of cell death. The major aim of this experiment is to assess the extent of cell death at early time points following injury in normal rabbit arteries and to determine to what extent the frequency of cell death is influenced by differences in balloon-to-artery ratio. Apoptosis is identified by a number of criteria including TUNEL staining, chromatin condensation, by the appearance of morphological features in electron micrographs at early time points, and by a loss of cellular density at later time points. These analyses are expected to yield quantitative data that relates the frequency of apoptosis to the degree of balloon overstretch.

For analyses of TUNEL labeling and chromatin condensation, the paraformaldehyde-fixed sections are incubated with TdT enzyme and dUTP conjugated to fluorescein and counterstained with Hoechst 33258 as described previously (Wang J, et al., 1997, Cancer Res. 57:351–354; Wang J and Walsh K. 1996; 273:359–361; Perlman, H., et al., 1997, Circulation 95:981–987). Signals are examined and photographed on a Nikon Diaphot microscope equipped with phase-contrast and epifluorescence optics. We have used prostates from castrated rats (T=3 days) as a positive control to develop procedures for analyzing apoptosis in the vessel wall (Columbel M, et al. Cancer Res. 1992; 52:4313–4319). The percentage of TUNEL-positive nuclei in arterial segments can be accurately determined by comparing the numbers of TUNEL-positive and Hoechst-positive nuclei. Approximately 100 nuclei are counted from each section. Cellular density is calculated for all injury time points and control vessels by counting the number of nuclei per area on a slide stained with hematoxylin and eosin as described previously (Perlman H, et al., 1997, Circulation 95:981–987). Employing these procedures, the effect of balloon size on the frequency of apoptosis is elucidated at early time points (30 min. and 4 hr.) and cell loss is elucidated at the late time point (3 days).

To confirm that the death is apoptotic, the glutaraldehyde-fixed sections are analyzed by transmission electron microscopy at the core facility at Tufts University using Philips CM-10 electron microscope as described previously (Perlman H, et al., Circulation 1997, 95:981–987). Apoptotic cell death is indicated by various morphological features including chromatin condensation that is localized to the edges of the nuclear membrane, while organelle membranes remain intact. The appearance of condensed chromatin in the Hoechst 33258 stain also provide evidence for apoptosis.

Immunohistochemical analyses of the apoptosis regulatory proteins is assessed with the methanol-fixed rabbit sections. Previously, we reported that injured rat carotid arteries displayed a decrease in bcl-X staining intensity in the most luminal layers of the media, while the immunostaining of bax did not appear to change upon injury. Similar analyses are also performed on the rabbit sections. The conditions for immunostaining for other apoptosis regulators including bad, bcl-2 and bag using prostates from castrated rats as a positive control have been determined and the expression patterns of these proteins also are assessed in the rabbit arterial sections. Finally, sections also are stained with antibodies to smooth muscle α-actin to identify VSMCs.

b) Double-injury model: In the second set of experiments apoptosis is studied in a double injury model. Throughout these experiments rabbits are maintained on a diet containing 1% cholesterol. Ten days after starting the diet a baseline angiogram is obtained. Then a 4F latex balloon catheter (Baxter) is advanced into the femoral artery from the left carotid artery to perform endothelial abrasion of the external iliac arteries (3 passages of the inflated balloon). Two weeks after the endothelial abrasion, a second balloon injury is performed on the left and right external iliac arteries using 2.5 mm or a 3.0 mm channel balloons as described above for the single-injury study. Vessels are harvested at time points (30 minutes, 4 hours, and 3 days post-injury; ~5 animals per time point). Control vessels are harvested from animals that have undergone endothelial abrasion, but not a second balloon injury. Portions of each vessel is then fixed for TUNEL staining, electron microscopy or immunohistochemistry as described above.

Analyses of cell death. Analyses of cell death and apoptosis regulatory protein expression is performed essentially as described above for the single-injury model. A major aim of this experiment is to assess the extent of cell death at early time points following injury in the neointimal versus the medial layer. It is possible that we may find different frequencies of apoptotic cell death in the medial versus neointimal smooth muscle cells in either the control vessels (single-injury, T=14 days) or in the vessels that have undergone a second injury. Of note, other investigators have found that VSMCs derived from atherosclerotic plaques undergo a higher frequency of apoptosis in vitro than cells derived from normal vessel (Bennett M R, et al., J. Clin. Invest. 1995; 95:2266–2274). It is anticipated that the experiments reveal differential expression of apoptotic regulatory proteins in the medial versus the neointimal VSMCs and/or differential regulation of these proteins following the second injury. Many differences have been noted between neointimal and medial VSMCs with regard to the expression of matrix, cell cycle, transcription factor, signaling and adherence genes (reviewed in Schwartz S M, et al., Circ. Res. 1995; 77:445–465). However, differential expression of apoptosis regulatory proteins in intimal versus medial VSMCs has not been reported.

Example 1 Results. Pilot experiments on a small number of rabbits were performed to determine the feasibility of the proposed experiments. In pilot experiments on the single-injury model, the frequency of TUNEL-positive cells at the 30 minute post-injury time point appeared to correlate with balloon size. A 1.20 to 1 balloon/artery ratio resulted in a relatively low frequency of TUNEL, positive cells that were confined to the most luminal layer of the media in the single injury model. On the other hand, a 1.44 to 1 balloon/artery ratio resulted in a higher frequency of apoptosis that extended into the deeper layers of the media.

In pilot experiments on the double-injury model, a relatively high frequency of TUNEL positive cells in the neointima and in the media was found with a 1.26 to 1 balloon/artery ratio. This is in contrast with the single injury result with a 1.20 to 1 ratio where a low frequency of TUNEL positive cells in the moist luminal layers was detected. We believe that the small balloon induced a relatively higher frequency of apoptosis in the double-injury model because the presence of neointimal tissue enhances the barotrauma to the vessel wall (the reference angiogram is obtained immediately prior to the first injury). Of particular note, analyses of cellular density in the double injury model (1.36 to 1 balloon/artery ratio) at the 3 day time point revealed markedly fewer cells in the media than in the neointima, suggesting that medial VSMCs are more sensitive to barotrauma-induced death. These findings evidence that the phenotypic modulation of VSMCs in vivo alters the sensitivity of these cells to stretch-induced apoptosis. Accordingly, one may correlate this difference in viability with differences in the expression patterns of the bcl-2 family proteins in the media versus the neointima.

Example 2.

Assess the effects of enhanced apoptosis on vessel lesion formation using a replication defective adenovirus encoding Fas ligand.

VSMCs, macrophages and T cells express Fas receptor and, therefore, are susceptible to Fas ligand-mediated cell death. An Adeno-FasL construct was utilized to characterize the differential effects of Fas ligand expression on endothelial cell and VSMC viability in vitro. This construct also is used to assess the effects of increased apoptosis on lesion formation in the rat carotid and rabbit iliac models of vascular injury. It is believed that the VSMCs engineered to express Fas ligand in effect behave as "immune privileged" cells. Accordingly, lesions are analysed for decreases in T cell and macrophage infiltration and an extended time course of transgene expression is observed.

To understand the role of apoptosis in vessel wall lesion formation and remodeling, a replication defective adenovirus encoding the FasL in models of vascular injury is used. Preparation of this adenovirus (designated "Adeno-FasL") is described above. Briefly, an Adeno-FasL construct was made by subcloning the FasL cDNA, mouse (Accession #U06948) (human FasL cDNA, Accession #U08137 (SEQ. ID NO.1 preferably is used in place of the mouse cDNA), downstream from an appropriate expression cassette (for example, the CMV promoter/enhancer) into the EcoRV site of the pCO1 vector containing the Ad5 adenoviral sequences required for homologous recombination. The resulting plasmid was linearized by restriction enzyme digestion and cotransfected in 293 cells with large ClaI fragment of the Ad5 dl324 viral DNA (Stratford-Perricaudet, L. D., et al., 1993, *J. Clin. Invest.* 90:626–630). The resulting replication-defective recombinant adenoviral constructs were purified from isolated plaques. The viral preparations were purified by two CsCl gradient centrifugations, dialyzed against buffer containing 10 mM Tris-Cl pH 7.5, 1 mM $MgCl_2$ and 135 mM NaCl and stored at $-80°$ C. in 10% glycerol. Viral titer was determined by plaque assay on 293 cells (Graham, F. L., and A. J. van der Eb, 1973, *Virology* 52:456–463) and expressed as plaque forming units (pfu) per ml.

The delivery of Adeno-FasL at the site of vascular injury creates a local region of a sustained apoptotic cell death. This, in effect, temporarily creates conditions similar to those found in "immune-privileged" tissues (e.g. eye and testis as well as some tumors) which express FasL and eliminate by apoptosis the Fas-bearing T cells that enter the tissue (French L E, et al., J. Cell. Biol. 1996; 133:335–343; Hahne M, et al., Science 1996; 274:1363–1366; Strand S, et al., Nature Med. 1996; 2:1361–1366; O'Connell J, et al., J. Exp. Med. 1996; 184:1075–1082). Furthermore, infection of the vessel wall with Adeno-FasL creates a "neighboring cell" effect in that the transduced, FasL-expressing VSMCs are catalysts for the apoptotic cell death of surrounding cells that express Fas receptor (VSMCs (infected or uninfected), macrophages and T cells).

Previous work on the intravascular delivery of Adeno-TK/gancyclovir has been shown to inhibit neointima formation (Ohno T, et al. Science 1994; 265:781–784; Guzman R J, et al., Proc. Natl. Acad. Sci. 1994; 91:10732–10736). This inhibition is presumed to result from a cytotoxic mechanism; however, VSMC apoptosis in vivo was not reported in these studies. The experiments described herein differ from the prior Adeno-TK/gancyclovir experiments in a number of key aspects: 1) The experiments herein involve the overexpression of an agent that is naturally found in atherosclerotic plaque, and therefore provides information about the endogenous regulatory pathways that are involved in the control of vascular cell viability. 2) It is reported that adenovirus-infected cells trigger a cellular immune response that leads to the destruction of the genetically modified cell (e.g., Yang Y, et al., Gene Ther. 1996; 3:137–144). However, when the VSMCs are engineered to express FasL they become resistant to immune attack due to their ability to eliminate through apoptosis the cytotoxic T-lymphocytes. Therefore, the time course of adenovirally-encoded FasL expression should greatly exceed that of other adenoviral transgenes. 3) The "neighboring cell" effect expected with Adeno-FasL will be functionally and mechanistically different from the "bystander" effect produced by TK/gancyclovir. The gancyclovir bystander effect is thought to result from the passage of a cytotoxic small molecule through gap junctions between homologous cells, but a FasL-expressing VSMC induces apoptosis in heterologous cells that express the Fas receptor (macrophages, T cells as well as VSMCs). 4) Previous studies have examined the effect of Rb overexpression on the vessel wall (e.g., Chang M W, et al., Science 1995; 267:518–522). Therefore, at a molecular level, the differential effects of cytotoxic versus cytostatic therapeutic strategies on the vessel wall are defined through a series of direct comparisons between Ad-FasL and Ad-Rb. Thus, the Ad-FasL has utility as a gene therapy reagent, as well as a research tool for understanding the consequences of apoptosis on lesion formation and vessel wall function.

Example 2 Materials and Methods:

An overview of the materials and methods for several of the procedures for preparing a replication-defective recombinant adenoviral vector containing the cDNA encoding FasL and delivering the recombinant viral vector by percutaneous arterial gene transfer are presented below.

Recombinant adenoviral vectors. Replication-defective recombinant adenoviral vectors, based on human adenovirus 5 serotype, were produced as previously described (Stratford-Perricaudet, L. D., et al., 1993, *J. Clin. Invest.* 90:626–630). The rat Gax gene cDNA was inserted between the XbaI and BamHI sites of the pCGN vector (Tanaka, M., and W. Herr, 1990, Cell 60:375–386) resulting in an in-frame fusion of the gax gene, starting at codon 2 of the putative open reading frame (Gorski, D H, et al., 1993, Mol. Cell. Biol. 13:3722–3733), to the N-terminal part of the influenza virus hemagglutinin (HA) epitope that is downstream from the cytomegalovirus (CMV) early promoter, herpes simplex virus and thymidine kinase gene 5' untranslated region (UTR). The XmnI-SfiI fragment from pCGN-Gax was then inserted at the EcoRV site of the pCO1 vector containing the Ad5 adenoviral sequence required for homologous recombination. The resulting plasmid was linearized by XmnI and cotransfected in 293 cells with the large fragment of the Ad5 dl324 viral DNA (Stratford-Perricaudet, L. D., et al., 1993, *J. Clin. Invest.* 90:626–630). The resulting replication-defective recombinant adenoviruses were purified from isolated plaques and viral DNA prepared. Recombinant adenoviruses containing the Gax cDNA were identified by restriction fragment analysis and amplified in 293 cells. The viral preparations used for both in vivo studies were purified by 2 CsCl gradient centrifugations, dialysed against buffer containing 10 mM Tris-Cl pH 7.5, 1 mM $MgCl_2$ and 135 mM NaCl and stored at −80° C. in 10% glycerol. Viral titer was determined by plaque assay on 293 cells as previously described (Graham, F L, and A J van der Eb, 1973, Virology 52:456–463) and expressed as plaque forming units 5 (pfu) per ml. The construction of the control Ad-βgal used in this work has been previously described (Stratford-Perricaudet, L. D., et al., 1993, *J. Clin. Invest.* 90:626–630).

Percutaneous arterial gene transfer and balloon angioplasty in vivo. Animal protocols were approved by St. Elizabeth's Medical Center Institutional Animal Care and Use Committee. The investigation conforms with the *Guide for the Care and Use of Laboratory Animals* published by the US National Institutes of Health (NIH Publication No. 85-23, revised 1985). New Zealand White rabbits (3.0–3.5 kg) (Pine Acre Rabbitry, Norton, Mass.) were anesthetized with ketamine (10 mg/kg) and acepromazine (0.2 mg/kg) following premedication with xylazine (2 mg/kg). In each rabbit a 2.0 cm long Channel balloon catheter (Boston Scientific, Watertown, Mass.) was introduced via the right common carotid and used to perform balloon angioplasty and arterial gene transfer. Balloon diameter was chosen to approximate a 1.3:1.0 balloon/artery ratio based on caliper measurement of magnified angiographic frames.

The angioplasty catheter was advanced to the lower abdominal aorta using a 0.014 in. Guidewire (Hi-Torque Floppy II, Advanced Cardiovascular Systems, Temecula, Calif.) under fluoroscopic guidance following reference angiography with 200 μg of nitroglycerin. The balloon catheter was then advanced into the external iliac artery immediately distal to the origin of the internal iliac artery where it was positioned using angiographic landmarks. Balloon inflation was then performed 3 times for 1 min each at 6 atm. The catheter was then inflated at nominal pressure and 200 μl of viral solution was instilled through the infusion port of the catheter. Infusion time was 60 sec. After 30 min. incubation, the balloon was deflated and the catheter was removed.

In each animal, iliac arteries were randomly assigned to be treated with either Ad-Gax ($4 \times 10^9$ pfu) or the β-galactosidase gene (Ad-βgal, $4 \times 10^9$ pfu) (Group 1, n-9). Alternatively, animals were treated with Ad-βgal or saline (Group 2, n-8). After treatment of one artery, a new balloon was used to treat the contralateral iliac artery. Before the procedure, heparin sodium (200 USP units, Elkins-sinn, Cherry Hill, N.J.) was administered intra-arterially. All animals received aspirin in water approximately 50 mg daily, from 3 days prior to the procedure until sacrifice.

Angioplasty and in vivo vasomotor reactivity. The angiographic luminal diameter of the iliac artery prior to gene transfer and prior to and after drug infusion, was determined using an automated edge-detection system (LeFree H T, et al., 1986, Proc. SPIE 626:334–341; Mancini G B J, et al., 1987, Circulation 75:452–460). Vasomotor reactivity of the arterial segment subjected to balloon angioplasty and arterial gene transfer was evaluated on the day of sacrifice. A 3 Fr., end-hole infusion catheter (Tracker-18™, Target Therapeutics, San Jose, Calif.) was inserted into the left carotid artery and advanced to the origin of transfected iliac artery using a 0.018 in. guidewire (Hi-Torque Floppy II) under fluoroscopic guidance. This catheter was used both for infusion of vasoactive drugs and selective angiography of the iliac artery. Angiography was performed immediately before and after each drug administration using 1 ml of non-ionic contrast media (Isovue-370, Squibb Diagnostics, New Brunswick, N.J.). Serial angiographic images were recorded on 105-mm spot film at a rate of 2 films per sec. for 4 sec. To assess endothelium-dependent vasomotor reactivity, acetylcholine chloride (Ach) or serotonin creatine sulfate (5-HT) were delivered from a constant infusion pump (1 ml/min) via the 3 Fr. Catheter at doses of 5 μg/kg/min for 2 min. Five minutes were allowed to elapse following each dose of agent to re-establish basal blood flow conditions. After administration of Ach and 5-HT respectively were completed, an identical protocol was employed to evaluate the contralateral artery. Finally, a single intra-aorta 200 μg of nitroglycerin was administered to assess endothelium-independent vasodilatation. The extent of the tone response was calculated as percent of maximal lumen diameter induced by nitroglycerin.

Evaluation of re-endothelialization and intimal hyperplasia. Following angiographic analysis and thirty minutes prior to sacrifice, all rabbits received an intravenous injection of 5 ml 0.5% Evans blue dye (Sigma) delivered via the ear vein. A cannula was inserted into the lower abdominal aorta and used to perfuse a total of 100 ml of 0.9% saline solution with 10 units/ml heparin in situ, followed by 100 ml of 100% methanol. The baseline angiogram recorded prior to balloon injury and the pilot radiographic recording of the angioplasty balloon were used to identify the arterial segment to be harvested. The injured segment of iliac artery was then dissected and incised longitudinally. The harvested arterial segment was pinned to a cork board, further fixed in 100% methanol, and photographed for planimetric analysis of reendothelialization. Tissues were further fixed by immersion in 100% methanol, embedded on longitudinal edge in paraffin, and cut in 5 μm sections onto slides coated with 3-aminopropyl-triethoxy-silane. The area of the intimal surface which was stained blue following application of Evans blue dye was interpreted to identify the portion of the arterial segment which remained endothelium-deficient. A computerized sketching program (MacMeasure version 1.9; NIMH, Bethesda, Md.) interfaced with a digitizing board (Summagraphics, Fairfield, Conn.) was used to outline the Evans blue positive and negative areas respectively. The extent of endothelialized area was calculated as a percent of the total intimal area encompassed within the 2 cm length of artery. Longitudinal histologic sections obtained from the 20 mm length of injured artery and stained with an elastic tissue trichrome stain were projected onto the digitizing board, and the area of the intima and media respectively were measured using the computerized sketching program described above. The thickness of the native media of the artery wall is variable reflecting in part the dimensions (diameter) of the individual rabbit iliac artery. Accordingly, thickness of the media was used to index the extent of neointimal thickening, and is thus stated as the ratio of intima to media area (I/M).

Statistical analysis. All results are expressed as mean±standard error (m±SE). Statistical significance was evaluated using a two tails. paired Student's t test for comparisons between two means in the same animal. A value of $p<0.05$ was interpreted to denote statistical significance.

Example 2 Experimental design:

a) In vitro experiments: The consequences of FasL on macrophage and T cell viability have been documented previously. This Example examines the viability of VSMCs and endothelial cells in response to infection with Adeno-FasL (a serotype 5 human replication defective adenovirus encoding the full-length murine Fas ligand cDNA from the CMV promoter/enhancer). VSMCs and endothelial cells are infected with different multiplicities of infection (MOI) and for different lengths of time, and the frequency of apoptosis is determined by FACS analysis. Related experiments examine the expression of FasL and Fas receptor on infected and noninfected VSMCs and endothelial cells.

In pilot experiments, we have compared the viability of rat VSMCs and bovine aortic endothelial cells infected with Ad-FasL. Control cells were infected with Ad-βgal or they were mock infected. Cells were infected at different MOIs for 4 hours, the media was then replaced, and cells were harvested 48-hours post-infection. FACS analysis revealed apoptosis (hypodiploid DNA) in the VSMC cultures that was dependent upon the dose of Ad-FasL. However, no evidence for apoptosis was detected in the endothelial cell cultures at any dose of virus tested (up to an MOI of 1000). Similarly, we have found that human VSMCs, but not human endothelial cells (HUVECs), are killed by infection with Ad-FasL indicating that the differential effect of FasL on cell viability is due to differences in cell type, and not species differences. Furthermore, using adenovirally-encoded reporter genes, we found that endothelial cells are transduced more efficiently than VSMCs. Thus we hypothesize that the lack of endothelial cell death results from the lack of Fas receptor expression.

To directly test the hypothesis that endothelial cells lack Fas receptor expression, Fas receptor and FasL immunodetection experiments were performed on cultured VSMCs and endothelial cells. First, Fas receptor expression was examined in cultured rat and rabbit VSMCs and endothelial cells. VSMCs are prepared in accordance with standard procedures known to one of ordinary skill in the art. See, e.g., Suzuki E, et al., Cytogenet. Cell. Genet. 1996; 73:244–249; Suzuki E, et al., Genomics 1996; 38:283–290. Aortic endothelial cells from rats and rabbit were prepared using the protocol of (Nicosia R F, et al., In Vitro Cell. Dev. Biol. 1994; 30A:394–399). Cells were harvested and incubated with anti-Fas monoclonal antibody (Transduction Laboratories, Lexington, Ky.) according to the directions of the manufacturer. This antibody recognizes Fas in multiple species including mouse and human. Cells were then incubated with a secondary fluorescein-conjugated goat antibody to mouse immunoglobulin, and immunofluorescence staining was analyzed by FACS analysis. We anticipated that these analyses will reveal Fas receptor expression in VSMC's, but not endothelial cells. To directly assay for FasL expression, Ad-FasL-infected and control-infected VSMC and endothelial cells are incubated with anti-Fas ligand monoclonal antibody (Transduction Laboratories), and immunofluorescence staining is analyzed by FACS analysis. We anticipate that FasL expression is detected in Ad-FasL-infected VSMCs and endothelial cells since adenoviral vectors are amphitrophic. However, Ad-FasL is only toxic to the VSMC cultures because endothelial cells do not express the receptor.

b) Experiments in rat carotid vessels: The rat carotid artery is used as a model of balloon denudation (Clowes A W, et al., Lab. Invest. 1983; 49:327–333) to test the effects of Ad-FasL on vascular lesion formation in vivo. The rat carotid model has been widely used to study stenosis following balloon injury. Rat carotid arteries are denuded with a balloon catheter and immediately exposed to different doses of Ad-FasL or control Ad-βgal virus or saline for 20 minutes under conditions described above (see materials and methods) (~10 animals per condition). Typically 1 EE9 viral pfu is delivered to each vessel because this has empirically been found to deliver the maximum transgene with no viral toxicity. Due to enhanced potency that may result from the "neighboring cell" effect, a range of doses for Ad-FasL: from ~1 EE6 to 1 EE9 pfu is examined. Rats are sacrificed two weeks later and quantitative morphometric analyses are performed on cross sections of the treated and control vessels. Apoptosis in these sections is assessed by the TUNEL technique and by chromatin condensation as described above. Adjacent sections are stained for SM-β-actin to identify VSMCs, HAM56 or CD68 mouse monoclonal antibodies to identify macrophages, and CD3 rabbit polyclonal antibody to identify T cells. FasL and Fas receptor expression is also determined immunohistochemically using the monoclonal antibodies described above. Depending upon results from the initial finding, longer and shorter time points are also examined. In particular, the analysis of Ad-FasL expression at late time points may be of particular interest because these cells likely evade the immune response that is elicited by the replication-defective adenovirus. On the other hand, early time points may provide more information on cell viability.

Example 2 Results: To test the feasibility of the proposed experiments, a pilot study on 15 rats treated with saline, 1 EE7 pfu. of Ad-FasL, or 1 EE8 pfu. Ad-FasL was performed. The injured, saline-treated vessels developed robust neointimal lesions with an I/M ratio of 1.56±0.17, similar to what we have found with Ad-βgal-treated vessels. Treatment with Ad-FasL had a dramatic impact on lesion formation. Ad-FasL at a dose of 1 EE7 pfu reduced the I/M ratio by 69%, and a dose of 1 EE8 reduced the I/M ratio by 79%. In comparison, Adeno-Rb reduces I/M ratio by 40% at a dose of 1 EE9 pfu (Chang M W, et al., Science 1995; 267:518–522). Based upon these data it appears that Ad-FasL is more effective than Rb, a cytostatic gene, even at 10- and 100-fold lower doses.

In the Ad-FasL-treated vessels we expect a higher frequency of apoptosis that is sustained for the length of adenoviral transgene expression (the typical span of adenoviral expression is 2 to 3 weeks). Expression may be maintained for much longer times because the FasL-expressing VSMCs are in effect "immune privileged" and therefore able to evade the immune response that is mediated by cytotoxic T lymphocytes, which are thought to be the major determinant of transient transgene expression from adenovirus. Accordingly, it is expected that fewer inflammatory cells are found in the tissue sections because such cells are eliminated by the Fas-mediated cell death. Due to the enhanced apoptosis in the Ad-FasL-treated vessels, it is expected that neointimal lesion formation is reduced, and this has been indicated by our experiments. Optionally, there is an accompanying thinning of the medial layer as detected in a decrease in medial area. With regard to a reduction in lesion formation, Ad-FasL is expected to be more potent than other adenovirally-delivered agents, such as the cytostatic Rb protein (Chang M W, et al., Science 1995; 267:518–522) due to the anticipated "neighboring cell" effect, and this is indicated by the working examples. Side-by-side dose-response comparisons with Adeno-Rb and Adeno-FasL is performed to directly address this issue. These experiments are expected to reveal an FasL expression on the outer diameter of the vessel, and provide further information regarding the role of apoptosis in vessel remodeling.

c) Experiments in rabbit iliac vessels: Based upon the finding in the rat carotid model of vascular injury, a more rigorous series of experiments in the rabbit models of vascular injury are performed. The rabbit model provides a number of advantages including the incorporation of hyperlipidemia and double-injury as described in Example 1. Furthermore, vessels can be analyzed for vasomotor reactivity and remodeling.

Initial experiments are performed to examine the effects of Ad-FasL on the balloon-injured iliac arteries of normal non-lipidemic rabbits. As described in Example 1, rabbit iliac arteries are injured with the inflation of a 2.5 mm channel balloon after a reference angiogram is obtained. Immediately after injury the same channel balloon is used to deliver Ad-FasL, Ad-βgal, or saline to the injured site as described above (see materials and methods). Each experimental condition involves 8 animals. Based upon our findings in the rat carotid model, an initial dose of FasL is chosen for its ability to induce robust apoptosis, but well below systemic toxicity. The systemic administration of 1 EE9 pfu of Ad-FasL will kill a rat, but we have found that this dose is tolerated in the carotid artery dwell technique because the viral solution is removed after a 20 minute incubation. (Due to the larger vessel size we typically deliver a 4-fold higher dose of adenovirus in the rabbit model than in the rat model.) In each rabbit, a baseline angiogram is obtained on the iliac artery and a 2.5 mm×2.0 cm long Channel balloon catheter is introduced via the right common carotid and used to perform balloon angioplasty (3 inflations for 1 min each at 6 atm.) and arterial gene transfer as described above (see materials and methods). Iliac arteries are examined 1 month later for lumen diameter, functional vasomotion, neointimal formation and reendothelialization. Subsequent experiments analyze different doses of Ad-FasL and earlier or later time points depending upon the initial results.

Angiography. Prior to sacrifice, angiographic luminal diameters of the iliac artery are determined using an automated edge-detection system (LeFree H T, et al., Proc SPIE 1986; 626:334–341; Mancini G B J, et al., Circulation 1987; 75:452–460). As described above (see materials and methods), a 3 Fr., end-hole infusion catheter is inserted into the left carotid artery and advanced to the origin of transfected iliac artery using a guidewire under fluoroscopic guidance. Angiography is performed immediately before and after each drug administration using 1 ml of non-ionic contrast media. Serial angiographic images are recorded on film at a rate of 2 films per sec. for 4 sec. To assess endothelium-dependent vasomotor reactivity, acetylcholine chloride (Ach) or serotonin creatine sulfate (5-HT) is delivered from a constant infusion pump (1 ml/min) via the catheter at doses of 5 μg/kg/min for 2 min. Five minutes are allowed to elapse following each dose of agent to re-establish basal blood flow conditions. After administration of Ach and 5-HT, respectively are completed, an identical protocol is employed to evaluate the contralateral artery (control). Finally, a single intra-aorta 200 μg of nitroglycerin is administered to assess endothelium-independent vasodilatation. The extent of the tone response is calculated as percent of maximal lumen diameter induced by nitroglycerin.

Re-endothelialization and morphological analyses. Following angiographic analysis and thirty minutes prior to sacrifice, rabbits receive an intravenous injection of 5 ml 0.5% Evans blue dye (Clowes A W, et al., Lab Invest. 1978; 39:141–150) delivered via the ear vein. A cannula is then inserted into the lower abdominal aorta and used for perfusion and tissue fixation. The injured 2-cm long segment of the iliac artery is then be dissected and incised longitudinally. The harvested arterial segment is pinned to a cork board and photographed for planimetric analysis of reendothelialization as described above (see materials and methods). Then tissues are embedded in paraffin, and cut into 5 μm longitudinal sections. These sections are stained with an elastic tissue triclrome stain and the area of the intima and media is measured with the computerized sketching program as described above. The thickness of the media is used to index the extent of neointimal thickening, and is thus stated as the ratio of intima to media area (I/M).

Alternatively, the harvested vessel are analyzed as cross sections to provide histological information about lumen diameter and other parameters. In particular the analysis of cross sections is expected to provide information about remodeling, reflected in changes in the circumference of the external elastic lamina, but analysis of cross sections would preclude us from analyzing the extent of re-endothelialization. However, serial intravascular ultrasound examination can be performed prior to animal sacrifice. Ultrasound assays provide information about the circumference of the external border of the media, and we have previously employed this technique to analyze the effects of Ad-Gax on the vessel wall.

Histology. Sections are stained by the TUNEL technique and Hoechst 33258 staining to assay for apoptosis. Adjacent sections are stained for SM-β-actin to identify VSMCs, HAM56 or CD68 mouse monoclonal antibodies to identify macrophages, and an appropriate antibody to identify T cells. FasL and Fas receptor expression is also determined immunohistochemically using the monoclonal antibodies described previously. Unlike dwell procedures of viral delivery in which the solution can be removed, significant viral dissemination is expected from the use of a channel balloon. To assess the effects of Ad-FasL dissemination, tissues are collected from contralateral non-transfected vessels liver, spleen, brain, testes, heart, lungs, ileum, kidneys and ipsilateral skeletal muscle and frozen in liquid nitrogen for subsequent analyses of cell death by TUNEL and viral dissemination by RT-PCR.

Double-injury model. Ad-FasL is then examined in the double injury model described in Example 1. In this set of experiments Ad-FasL is introduced at the time of the second injury, and vessels are harvested for analysis one month later as described above. We have observed in the working examples that neointimal cells appear to be more highly resistant to stretch-induced cell death than medial VSMCs (see Example 1). However, in the experiments of this Example, the neointimal VSMCs are expected to have a greater exposure to the Ad-FasL leading to their death.

Example 2 Results. We expect that the Ad-FasL-treated vessels display a higher frequency of apoptosis than the control vessels and as a result a larger lumen diameter and a reduction in I/M ratio is observed in both the single and double injury models. Since endothelial cells lack Fas receptor, Ad-FasL-treatment does not alter the rate of reendothelialization. As mentioned previously, histological analyses reveals fewer inflammatory cells due to the "immune privileged" characteristics of the treated vessel and, as a result, expression of the FasL transgene is detected at relatively late time points because the FasL-expressing VSMCs evade immune detection. Finally, the increase in apoptosis mediated by Ad-FasL perturbs the remodeling process. For example, an increase in outer diameter of the Ad-FasL-treated vessel relative to control indicates that apoptosis inhibits the constrictive remodeling process.

Example 3.

Characterize apoptosis in a mouse model of arterial injury.

In a reproducible model of lesion formation in murine carotid arteries, apoptotic cell death is examined using a number of biochemical and morphological criteria. Immunohistochemical analyses of arterial sections document changes in the expression of apoptosis regulatory proteins. These measurements permit the use of transgenic and gene disruption technologies to assess the role of apoptosis regulatory proteins in vessel wall lesion formation.

The characterization of a murine model of injury-induced apoptosis in blood vessels has enormous utility because transgenic and gene disruption technologies can be employed to understand the regulation and role of apoptosis in the vessel wall. The findings from these studies provide fundamental information about the role of VSMC apoptosis in the regulation of lesion size and vessel wall remodeling. The goal of these experiments is to identify and characterize the frequency of VSMC apoptosis in a reproducible model of murine vascular injury.

Numerous studies in rat, rabbit and baboon have demonstrated that a reduction in blood flow will lead to constrictive remodeling and intimal hyperplasia. Recently we employed a similar model in mouse that was developed by Volkhard Lindner (The Molecular Biology of the Cardiovascular System: Keystone, Colo. Keystone Symposia 1996; 66 (abstract)). This procedure involves the ligation and complete cessation of blood flow through the mouse carotid artery. In C57 mice the ligation of the vessel prior to the carotid bifurcation results in reproducible neointima formation at 4 weeks. It is striking that this injury decreases the circumference of the external elastic lamina, indicating that the vessel had undergone constrictive remodeling. We have also compared lesions formed by this method in C57 wild-type mice with C57 mice null for ApoE, an apolipoprotein whose absence leads to elevated plasma cholesterol levels and spontaneous atherosclerotic lesions in mice (Plump A S, et al., Cell 1992; 71:343–353). We observed a far more robust lesion in the ApoE-/-mice. Histological staining revealed that the lesions primarily consist of VSMCs. Staining with rat anti-mouse F4/80 antigen revealed 1 to 2 macrophages per section in the C57 mice and 2 to 8 macrophages per section in the ApoE-/-mice (predominantly in the neointima and rarely in the media). Collectively these data demonstrate the utility of the ligation model for studying role of apoptosis in vessel lesion formation using a mouse genetics approach. The changes in vessel wall thickness and constrictive remodeling observed in this model are believed to be relevant to the pathophysiologies associated with flow reduction.

Experimental design: The carotid arteries of C57 mice (~10 mice per time point) are exposed and ligated with a surgical silk suture immediately below the carotid bifurcation. 24 hours prior to sacrifice mice are injected with 1 mg of BrdU for subsequent analyses of cell proliferation. At various times (T=1, 3, 7, 14, 28, and 56 days) the mice are killed and the ligated and contralateral control vessels are harvested and fixed in paraformaldehyde or methanol. Embedded vessels are sectioned and subjected to morphometric analyses, analyses of apoptosis, determination of medial and neointimal cell number, and staining for apoptosis regulatory proteins.

Morphometric analyses. Sections from harvested vessels are characterized morphometrically to assess how the frequency of apoptosis correlates with lesion geometry. A computerized sketching program interfaced with a digitizing board are used to determine the circumference of the external elastic lamina, the internal elastic lamina, and the lumen. From these values the areas of the media, the neointima and the lumen can be calculated. Intimal hyperplasia is reflected in the values of intimal area and by the intima to media (I/M) ratio. Changes in the circumference of the external elastic lamina are used as an indication of remodeling.

Analyses of apoptosis. The purpose of this Example is to assess the frequency of apoptosis at various time points after ligation of the vessel. The frequency of apoptosis is determined by TUNEL staining as described above. The percentage of TUNEL-positive nuclei in the media or neointima of arterial segments can be determined by comparing the numbers of TUNEL-positive and Hoechst-positive nuclei. To confirm that the death is apoptotic, glutaraldehyde-fixed sections are analyzed by transmission electron microscopy as described previously (Perlman H, et al., Circulation 1997, 95:981–987). The appearance of condensed chromatin in the Hoechst 33258 stain also provides evidence for apoptosis.

Determination of cell number and cell proliferation. Cellular density are calculated in for all time points and for control vessels by counting the number of nuclei per area on a slide stained with hematoxylin and eosin as described previously (Perlman H, et al., Circulation 1997, 95:981–987). The proliferative index are determined by immunostaining for BrdU.

Detection of apoptosis regulatory proteins. Immunohistochemical analyses of the apoptosis regulatory proteins are assessed with the methanol-fixed sections. Previously we reported that injured rat carotid arteries displayed a decrease in bcl-X staining intensity in the most luminal layers of the media, while the immunostaining of bax did not appear to change upon injury (Perlman H, et al., Circulation 1997, 95:981–987). Similar analyses are also performed in this mouse model of vascular injury.

The expression of other apoptosis regulatory proteins including Bad, Bcl-2 and Bag, and in the mouse vessels also is determined by immunostaining in accordance with published procedures. In particular we are interested in determining whether the expression of these proteins differs between cells in the medial and neointimal layers. Finally, sections are also stained with antibodies to smooth muscle β-actin to identify VSMCs, rat anti-mouse F4/80 antigen to identify macrophages, and CD4 rat IgG to identify T cells (Zhou X, et al., Am. J. Pathol. 1996; 149:359–366).

Example 3 Results. As mentioned above, reproducible neointimal formation and constrictive remodeling in the ligated vessels relative to contralateral controls in C57 mice was observed at 28 days. The working examples also involved a small number of animals that were tested for fragmented chromatin. TUNEL-positive nuclei with a pyknotic appearance were detected in the media and neointima of the ligated vessels, suggesting that cells were undergoing apoptotic cell death. From these working examples, it appears that more TUNEL-positive nuclei were detected in the neointima than in the media. An analysis of the control vessels revealed only a single TUNEL-positive medial cell in the 10 sections examined from individual mice. A higher frequency of TUNEL-positive cells were found in the neointima of the ApoE-null mice which displayed more robust lesions. Thus it appears that the frequency of TUNEL-positive cells roughly correlates with lesion size at 28 days. As expected, the frequency of TUNEL positive cells at 28 days was low relative to the apoptosis that occurs within hours of balloon injury in the rat and rabbit models. It is possible that lesion formation is near completion in the ligated mouse vessels at I month and that a low rate of proliferation is in balance with a low rate of apoptosis. The experiments of this Example provide information regarding the regulation of apoptosis in the vessel wall.

Example 4.

Study the mechanisms that coordinate cell cell cycle and apoptosis at a molecular level.

The distention of the vessel wall by balloon angioplasty triggers proliferation and apoptosis in VSMCs. Accordingly, injury-induced apoptosis may be modulated, in part, by the cellular response to proliferative signals under conditions of mechanical stress. The experiments of this Example examine how apoptosis and cell cycle are coordinated at a molecular level. These findings provide a foundation for understanding the mechanisms that regulate apoptosis in the vessel wall and broadly relate to other systems where proliferating cells undergo apoptosis.

A series of in vitro experiments are planned to study the coordination of cell cycle and apoptosis. These experiments provide experimental evidence to establish that E2F and p21 function in a negative feedback loop to control cell cycle and apoptosis.

Recently we have obtained data indicating that E2F1 and p21 function in a negative feedback loop. The data indicate that the E2F1 transcription factor transactivates the p21 promoter. Increased p21 expression decreases pRb phosphorylation which in turn results in the inactivation of E2F. Presumably this regulatory mechanism functions to maintain E2F at a safe levels so apoptosis will not be induced as the cell cycle is traversed. The hypothesis that E2F and p21 function in a negative feedback loop is consistent with some previous observations that appeared paradoxical at first glance: 1) It has been reported that p21 can be induced by serum (Michieli P, et al., Cancer Res. 1994; 54:3391–3395). Since serum will active the Cdks and cell growth, the observed serum induction of the p21 growth inhibitor seems contradictory 2). It is also paradoxical that E2F1-null mice develop proliferative disorders (Field S J, et al., Cell 1996; 85:549–561; Yamasaki L, et al., Cell 1996; 85:537–548) and this observation has led others to speculate that growth inhibitors may be included in the repertoire of genes regulated by E2F1 (Weinberg R A. Cell 1996; 85:457–459).

To test for the potential involvement of a feedback loop, we assayed the effect of E2F overexpression on p21 expression. Treating cells with replication defective adenovirus expressing E2F1 (provided by J. DeGregori and J. R. Nevins, (DeGregori J, et al., Mol. Cell Biol. 1995; 15:4215–4224) resulted in a substantial upregulation of p21 expression at the level of protein and mRNA. This upregulation was also detected in p53−/− fibroblasts, but not in p21−/− fibroblasts, indicating the specificity of the assay. The rrlagnitude of the p21 upregulation by E2F1 exceeded that obtained by the serum stimulation of these cells. Since E2F1 is a transcription factor, we tested whether an E2F1 expression plasmid would activate the p21 promoter in a transfection assay. Co-transfection with wild-type E2F1 activated the 2.4 Kbp promoter construct by 10-fold. This activation did not require the p53 responsive element located at position −2.35 Kbp (El-Deiry W S, et al., Cell 1993; 75:817–825), but a minimal 300 bp promoter fragment was not activated by E2F1. Furthermore, deletion of the E2F1 transcriptional activation domain abolished the upregulation. We have also found that serum stimulation of quiescent cells activated the 2.4 and 2.3 Kbp promoter constructs. These observations support our hypothesis that p21 and E2F function in a negative feedback loop, and that the observed serum induction of p21 is the direct consequence of E2F action on the p21 promoter. The following experiments are performed to confirm this hypothesis:

To identify the site of E2F1 action in the p21 promoter, a series of unidirectional deletion mutations in the 2.3 Kbp promoter fragment are constructed in a luciferase reporter plasmid. These constructs are tested for their ability to be trans-activated by an E2F1 expression plasmid. In another set of experiments, the same constructs are tested for the ability of serum stimulation to upregulate the expression of the luciferase reporter gene. If the hypothesis that E2F1 mediates the serum-induction of p21 is correct then we should observe parallel behavior of this constructs with regard to their ability to be induced by E2F1 and by serum. It is likely the activation of p21 transcription will occur through an E2F1 binding site [consensus=TTT(G/C)(G/C) CG(G/C)]. A number of candidate E2F regulatory elements can be found in the p21 promoter sequence due to the relatively low complexity of the consensus sequence. Once p21 promoter fragments that contain the E2F1 and/or serum responsive sites are identified by the mutational analysis, duplex oligonucleotides corresponding to this region or regions are synthesized and tested for their ability to bind to E2F in an electrophoretic mobility shift assay. If the E2F1 and/or serum responsive elements do not bind to E2F, these data indicate more complex interaction, such as the activation of an intermediary transcription factor by these agents.

To understand the functional consequences of the proposed E2F/p21 feedback loop, the effect of E2F1 overexpression on cyclin dependent kinase activity in p21−/− mouse embryonic fibroblasts is compared relative to that in isogenic wild-type fibroblasts. Growing cells are infected for 4 hours with Ad-E2F1 or the Ad-βgal control at an multiplicity of infection of 300 that results in >90% transduction efficiency. After 18 hrs. extracts are prepared to assay for Cdk2-histone kinase activity and Cdk4 Rb-kinase activity using the methods described previously by my laboratory (Guo K, et al., Mol. Cell. Biol. 1995; 15:3823–3829; Wang J and Walsh K., Cell Growth & Diff. 1996; 7:1471–1478). Assuming the negative feedback loop is functional, it is expected that the infection with Ad-E2F1 will reduce Cdk activity and that this reduction in activity is greater in p21+/+ cells than in p21−/− cells. Interpretation of this experiment may be complicated by the ability of E2F1 overexpression to induce apoptotic cell death. However, it is likely that this is a minimal problem because: 1) E2F1 overexpression kills quiescent, not growing cells, 2) early time points are examined before significant cell death commences, and 3) we can control for cell death, if it occurs, by analyzing for differences in Cdk activity between the two types of cells. Another potential complication is that E2F1 will induce cyclin A and cyclin E which will activate Cdk2 histone kinase activity (DeGregori J, et al., Mol. Cell Biol. 1995; 15:4215–4224). However, assuming the proposed feedback loop is functional, it is expected that the magnitude of the Cdk2 induction is less in the p21−/− cells. Also, this complication would not affect the Cdk4 pRb kinase activity which we can also assay as described previously (Wang J and Walsh K., Cell Growth & Diff. 1996; 7:1471–1478). In addition, immunoprecipitation-coupled immunoblot experiments are performed to demonstrate that under conditions of E2F1 overexpression there is an enhanced association of p21 with the Cdk2 and Cdk4 complex using published procedures (Wang J and Walsh K., Cell Growth & Diff. 1996; 7:1471–1478).

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims.

All references, patents and patent publications that are recited in this application are incorporated in their entirety herein by reference.

A Sequence Listing is presented below and is followed by what is claimed.

I claim:

1. A method for treating a condition characterized by excessive vascular proliferation of smooth muscle cells in a subject otherwise free of symptoms calling for Fas ligand treatment comprising:

locally administering a nucleic acid molecule encoding a Fas ligand polypeptide to a subject in need of such treatment in an amount effective to inhibit excessive vascular smooth muscle cell proliferation in a subject.

2. The method of claim 1, wherein the nucleic acid molecule encoding a Fas ligand polypeptide is a nucleic acid encoding a Fas ligand polypeptide selected from the group consisting of:

(a) an intact Fas ligand polypeptide;

(b) a soluble Fas ligand polypeptide; and (c) a membrane-associated Fas ligand polypeptide.

3. The method of claim 2, wherein the intact Fas ligand polypeptide has an amino acid sequence of SEQ. ID NO.2.

4. The method of claim 1, wherein the condition is selected from the group consisting of:

(a) a vascular injury which results in smooth muscle cell proliferation;

(b) vein graft occlusion;

(c) pulmonary vascular remodeling characterized by smooth muscle cell proliferation; and (d) cardiovascular remodeling characterized by smooth muscle cell proliferation.

5. The method of claim 4, wherein the vascular injury is restenosis following balloon angioplasty.

6. A method for treating a subject who has sustained a vascular injury comprising:

locally administering a nucleic acid encoding a Fas ligand polypeptide to a subject in need of such treatment in an amount effective to inhibit vascular smooth muscle cell proliferation, wherein the subject is otherwise free of symptoms calling for Fas ligand nucleic acid treatment.

7. The method of claim 6, wherein the vascular injury is restenosis following balloon angioplasty.

8. The method of claim 6, wherein the nucleic acid molecule encoding a Fas ligand polypeptide is administered to a subject with an arterial occlusion in conjunction with treatment of said occlusion.

9. A method for inhibiting vascular remodeling in a subject otherwise free of symptoms calling for Fas ligand treatment, comprising:

locally administering a nucleic acid encoding a Fas ligand polypeptide to a subject in need of such treatment in an amount effective to inhibit vascular remodeling, wherein the subject is otherwise free of symptoms calling for treatment with a Fas ligand nucleic acid.

* * * * *